(12) United States Patent
MacMillan

(10) Patent No.: US 6,552,226 B1
(45) Date of Patent: Apr. 22, 2003

(54) TANDEM ACYL-CLAISEN REARRANGEMENT IN THE PREPARATION OF CHIRAL PRODUCTS

(75) Inventor: David W. C. MacMillan, Pasadena, CA (US)

(73) Assignee: The Regents of the University of California, Oakland, CA (US)

( * ) Notice: Subject to any disclaimer, the term of this patent is extended or adjusted under 35 U.S.C. 154(b) by 3 days.

(21) Appl. No.: 09/670,861

(22) Filed: Sep. 26, 2000

(51) Int. Cl.⁷ .................... C07C 233/00; C07C 235/00; C07C 237/00; C07C 239/00; C07C 69/52

(52) U.S. Cl. .................. 564/205; 558/251; 558/257; 560/193; 560/205; 564/142; 564/143; 564/152; 564/160; 564/161; 564/162

(58) Field of Search .................. 558/251, 257; 560/193, 205; 564/142, 143, 152, 160, 161, 162, 163, 205

(56) References Cited

U.S. PATENT DOCUMENTS 6,359,174 B1 * 3/2002 MacMillan et al. ......... 564/142

OTHER PUBLICATIONS

Blechert (1989), "The Hetero–Cope Rearrangement in Organic Synthesis," *Synthesis* 2:71–82.
Corey et al. (1991), "Highly Enantioselective and Diastereoselective Ireland–Claisen Rearrangement of Achiral Allylic Esters," *J. Am. Chem. Soc.* 113(10):4026–4028.
Corey et al. (1995), "Enantioselective Total Synthesis of β–Elemene and Fuscol Based on Enantioconrolled Ireland–Claisen Rearrangement," *J. Am. Chem. Soc.* 117(1):193–196.
Deur et al. (1996), "Photochemical Reaction Between Tertiary Allylic Amines and Chromium Carbene Complexes: Synthesis of Lactams via a Zwitterion Aza Cope Rearrangement," *J. Org. Chem.* 61(8):2871–2876.
Diederich et al. (1995), "Synthesis of Optically Active Nine–Membered Ring Lactams by a Zwitterionic Aza–Claisen Reaction," *Angew. Chem. Int. Ed. Engl.* 34(9):1026–1028.
Edstrom (1991), "New Methodology for the Synthesis of Functionalized Indolizidine and Quinolizidine Ring Systems," *J. Am. Chem. Soc.* 113(17):6690–6692.
Enders et al. (1996), "Asymmetric [3.3]–Sigmatropic Rearrangements in Organic Synthesis," *Tetrahedron: Asymmetry* 7(7):1847–1882.
Hiratani et al. (1995), "Double Claisen Rearrangement: A New Route to Novel Ligands for Metal Ions," *Tetrahedron Letters* 36(31):5567–5570.
Hiratani et al. (1997), "Tandem Claisen Rearrangement: A Novel, One–Step Synthesis of Calixarene Analogues From Macrocyclic Polyethers," *J. Am. Chem. Soc.* 119(51):12677–12678.
Hiratani et al. (1997), "Synthesis of Novel Crownophanes Containing Two Phenolic Moieties via a Tandem Claisen Rearrangement," *Tetrahedron Letters* 38(52):8993–8996.
Ishida et al. (1989), "A Convenient and Regioselective Synthesis of 4,6–Diaryl–2,3,4,7–Tetrahydrooxepin–2–ones and 1,4–Diphenyl–2,3,4, 7–Tetrahydro–1H–Azepin–2–One," *Synthesis* 7:562–564.
Kallmerten et al. (1989), "Recent Applications of Sigmatropic Reactions to the Synthesis of Highly–Oxygenated Natural Products," *Stud. Nat. Prod. Chem.* 3:233–285.
Kim et al. (1993), "One–Pot Syntheses of 2,3–Dihydro–2, 2–Dimethylbenzofuran Derivatives," *Heterocycles* 36(3):497–505.
Kunng et al. (1983), "A Novel Synthetic Approach to Reserpine Based Upon Amino–Claisen Rearrangements of Zwitterionic N–Vinylisoquinuclidenes," *J. Org. Chem.* 48(23):4262–4266.
Malherbe et al. (1978), "A New Type of Claisen Rearrangement Involving 1,3–Dipolar Intermediates," *Helvetica Chimica Acta* 61(295):3096–3099.
Malherbe et al. (1983), "Reations of Haloketenes With Allyl Ethers and Thioethers: A New Type of Calisen Rearrangement," *J. Org. Chem.* 48(6):860–869.
Mandai et al. (1991), "A New Stereoselective Synthetic Method for Bicyclo[3.3.0]Octane Framework," *Tetrahedron Letters* 32(28):3399–3400.
Maruoka et al. (1990), "Asymmetric Claisen Rearrangement Catalyzed by Chiral Organoaluminum Reagent," *J. Am. Chem. Soc.* 112(21):7791–7793.
Maruoka et al. (1995), "Molecular Design of a Chiral Lewis Acid for the Asymmetric Claisen Rearrangement," *J. Am. Chem. Soc.* 117(3):1165–1166.
Maurya et al. (1992), "Some Unexpected Reactions Involving Diphenylketene," *J. Chem. Soc. Perkin Trans.* 1:1617–1621.
Mikami et al. (1990), "Asymmetric Tandem Claisen–Ene Strategy for Steriod Total Synthesis: An Efficient Access to (+)–9(11)–Dehydroestrone Methyl Ether," *J. Am. Chem. Soc.* 112(10):4035–4037.

(List continued on next page.)

Primary Examiner—Richard L. Raymond
Assistant Examiner—Zachary C. Tucker
(74) Attorney, Agent, or Firm—Reed & Associates

(57) ABSTRACT

A novel tandem acyl-Claisen rearrangement reaction is provided. An allylic reactant such as an allylic amine or an allylic thioether, having at least two functional groups that enable the reactant to undergo at least two successive Claisen rearrangement reactions, is reacted with an acid chloride in the presence of a Lewis acid catalyst composition composed of a Lewis acid and a second catalyst component selected from the group consisting of tertiary amines and non-nitrogenous bases. The stereochemistry of the reaction product is readily controlled by the positioning and size of substituents on the allylic reactant. The reaction may be carried out on a solid support, i.e., on the surface of a substrate suitable for conducting solid phase chemical reactions.

41 Claims, No Drawings

OTHER PUBLICATIONS

Mikami et al. (1994), "Asymmetric Tandem Claisen–Ene Strategy for Convergent Syntehsis of (+)–9(11)–Dehydroestrone Methyl Ether: Stereochemical Studies on the Ene Cyclization and Cyclic Enol Ether Claisen Rearrangement for Steriod Total Synthesis," *J. Am. Chem. Soc.* *116*(24):10948–10954.

Moody (1987), "Claisen Rearrangements in Heteroaromatic Systems," *Advances in Heterocyclic Chemistry 42*:203–244.

Mori et al. (1984), "Organoaluminium Assisted Rearrangements of Five–Membered Ring Enol Ethers With Vinyl Substituents," *Tetrahedron 40*(20):4013–4018.

Rosini et al. (1981), "Reaction of Dichloroketene With Cyclic Thioketals of α,β–Cycloalkenones: Syntehsis of 1,7–Dithiacycloalk–5–En–2–One Derivatives by a Four–Carbon Cycloenlargement," *J. Org. Chem.* *46*(11):2228–2230.

Saito et al. (1996), Aluminum Tris(4–Bromo–2,6–Diphenylphenoxide)(ATPH–Br): An Effective Catalyst for Claisen Rearrangement, *Synlett 8*:720–722.

Stevenson et al. (1982), "A 1,5–Diene Synthesis via Titanium and Aluminum Mediated Reactions," *Tetrahedron Letters 23*(31):3143–3146.

Takai et al. (1981), "Aliphatic Claisen Rearrangement Promoted by Organoaluminium Compounds," *Tetrahedron Letters 22*(40):3985–3988.

Thyagarajan et al. (1967), "Stereoselectivity in a Para Claisen Rearrangement: 1,4–Di–(2,6–Dimethylphenoxy)–Cis and Trans–But–2–enes," *Chemistry and Industry*, pp. 401–402.

Tokuhisa et al. (1999), "Synthesis of Chiral Crownophanes via Tandem Claisen Rearrangement," *Tetrahedron Letters 40*:8007–8010.

Uzawa et al. (1998), "Lewis–Acid–Assisted 'Tandem Claisen Rearrangement': Application to the Synthesis of a New Type of Macrocycle Containing Phenolic Moieties," *Chemistry Letters 4*:307–308.

Vedejs et al. (1994), "Aza–Claisen Rearrangements Initiated by Acid–Catalyzed Michael Addition," *J. Am. Chem. Soc.* *116*(2):579–588.

Wang et al. (1998), "Complexation of Fullerenes with Bis–Calix[n]Arenes Synthesized by Tandem Claisen Rearrangement," *J. Am. Chem. Soc. 120*(47):12226–12231.

Weiss et al. (1967), "Dérivés αα'–Disubstitués de L'isobutène: Double Transposition de Claisen des αα'–Bis–Aryloxy–Isobutènes," *Bull. Soc. Chem. Fr.* 34(6):2033–2038.

Yoon et al. (1999), "Development of a New Lewis Acid–Catalyzed Claisen Rearrangement," *J. Am. Chem. Soc. 121*(41):9726–9727.

Ziegler (1988), "The Thermal, Aliphatic Claisen Rearrangement," *Chemical Reviews 88*(8):1423–1452.

* cited by examiner

TANDEM ACYL-CLAISEN REARRANGEMENT IN THE PREPARATION OF CHIRAL PRODUCTS

TECHNICAL FIELD

The present invention relates generally to synthetic organic chemistry. More particularly, the invention relates to the Claisen rearrangement reaction and to a novel method of performing such reactions in tandem so as to give rise to chiral products. The invention finds utility in the fields of organic synthesis and stereospecific catalysis.

BACKGROUND

Since its discovery in 1912, the Claisen rearrangement has become one of the most powerful tools for carbon-carbon bond formation in chemical synthesis. See, e.g., Claisen (1912) *Chem. Ber.* 45:3157; Enders et al. (1996) *Tetrahedron: Asymmetry* 7:1847; Blechert et al. (1989) *Synthesis* 71; Kallmerten et al. (1989) *Stud. Nat. Prod. Chem.* 3:323; Moody et al. (1987) *Adv. Heterocycl. Chem.* 42:203; and Ziegler et al. (1988) *Chem. Rev.* 88:1423. The Claisen reaction is a [3,3]-sigmatropic rearrangement, which involves the conversion of an allylic compound, generally an allylic vinyl ether, to an α,β-disubstituted, β,γ-unsaturated carbonyl compound. The reaction may be illustrated as follows:

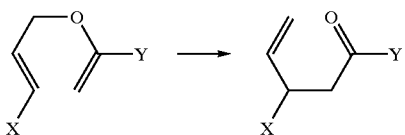

Allylic aryl ethers also undergo a Claisen rearrangement to give ortho-allylphenols:

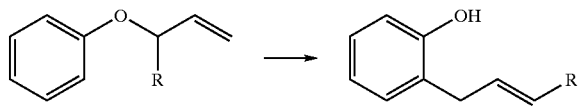

Activation of Claisen reactions has traditionally been accomplished under thermal control, typically at temperatures of 200° C. or more. Activation has also been achieved through the incorporation of cationic or anionic charge in the bond reorganization event (see Takai et al. (1981) *Tetrahedron Lett.* 22:3985; Takai et al. (1984) *Bull. Chem. Soc.* 57:446; Stevenson et al. (1982) *Tetrahedron Lett.* 23:3143; and Takai et al. (1984) *Tetrahedron* 40:4013; Arnold et al. (1949) *J. Am. Chem. Soc.* 71:1150; Ireland et al. (1973) *J. Am. Chem. Soc.* 94:5897; Denmark et al. (1982) *J. Am. Chem. Soc.* 104:4972; Wilson et al. (1984) *J. Org. Chem.* 49:722; Buchi et al. (1985) *J. Org. Chem.* 50:4664; and Alker et al. (1 990) *J. Chem. Soc. Perkins Trans.* 1, 1623). Despite its prolific use in chemical synthesis, very few examples of catalytic Claisen variants have been reported. See Vedejs et al. (1994) *J. Am. Chem. Soc.* 116:579, pertaining to protic acid (e.g., toluenesulfonic acid) catalysis of a Michael addition reaction, in turn initiating an aza-Claisen rearrangement. See also Saito et al. (1996) *Synlett*, 720, which describes the use of an aluminum catalyst, aluminum tris(4-bromo-2,6-diphenylphenoxide), in the Claisen rearrangement of allyl vinyl ethers.

In 1978, Bellus and Malherbe reported a ketene-Claisen reaction, in which treatment of an allyl ether with dichloroketene was found to result in the formation of a 1,3-dipolar allyl vinyl ether, which subsequently underwent [3,3]-bond reorganization, as follows:

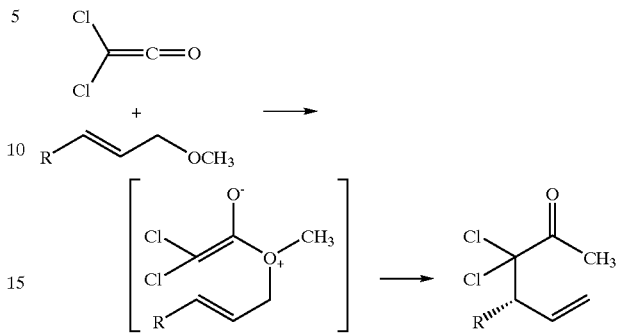

(Malherbe et al. (1978) *Helv. Chim. Acta* 61:3096; Malherbe et al. (1983) *J. Org. Chem.* 48:860). Subsequently, others have demonstrated utility of tertiary allylic amines in analogous [3,3]-sigmatropic rearrangement reactions. Edstrom et al. (1991) *J. Am. Chem. Soc.* 113:6690; Kunng et al. (1983) *J. Org. Chem.* 48:4262; Maruya et al. (1992) *J. Chem. Soc., Perkin Trans*, 1617; Vedejs et al., supra; Diederich et al. (1995) *Angew Chem., Int. Ed. Engl.* 34:1026; Deur et al. (1996)*J. Org. Chem.* 61:2871).

The aforementioned reactions are limited because of the ketene reactant used, as ketenes are highly unstable compounds. Furthermore, prior syntheses are generally not enantioselective; those who have attempted enantioselective Claisen rearrangements have met with substantial difficulties. For example, Corey et al. (1996), *J. Am. Chem. Soc.* 118:1229, developed an enantioselective Claisen reaction of an allylic ester, but the synthesis required a reaction time of fourteen days. Yamamoto et al. (1995), *J. Am. Chem. Soc.* 117:1165, also developed an enantioselective Claisen reaction for rearrangement of an allylic vinyl ether, but the synthesis required stoichiometric quantities of an aluminum promoter.

Applicant's commonly assigned U.S. patent application Ser. No. 09/670,863 for "Lewis Acid-Catalyzed Claisen Rearrangement in the Preparation of Chiral Products," filed on even date herewith, now U.S. Pat. No. 6,359,174, addresses the aforementioned need in the art for an improved Claisen reaction that proceeds quickly, can be conducted as a "one-pot" synthesis, is activated using catalytic quantities of a catalytic composition, and can be used to produce chiral products in enantiomerically pure form. The present invention provides a similar "one-pot" synthetic process wherein catalyzed Claisen rearrangement reactions proceed in tandem to produce enantiomerically pure chiral products.

Claisen rearrangements have previously been conducted in tandem with various other reactions. For example, Thyagarajan et al. (1967) *Chemistry and Industry*, pp. 401–402, report the use of Claisen rearrangements in conjunction with Cope rearrangements. Claisen-cyclization rearrangements are discussed by Kim et al. (1993) *Heterocycles* 36(3):497–505 and Weiss et al.(1967) *Bull. Soc. Chim. Fr.* 34:2033–2038. Tandem Claisen-ene rearrangements have been developed by Mikami et al.; see Mikami et al. (1990) *J. Am. Chem. Soc.* 112:4035–4037, and Mikami et al. (1994) *J. Am. Chem. Soc.* 116:10948–10954. Mandai et al. (1991) *Tet. Lett.* 32(28):3399–3400 present a Claisen-aldol rearrangement for use in synthesizing a bicyclo [3.3.0] octane framework.

Successive double Claisen rearrangements (i.e., "tandem" Claisen reactions) have been developed by Hiratani et al. in the synthesis of chelating agents for metal ions. That is, Hiratani et al. (1995), *Tet. Lett.* 36:5567–5570, and Hiratani et al. (1997), *Tet. Lett.* 38:8993–8996, describe a tandem Claisen rearrangement in the synthesis of crownophanes (macrocycles containing rigid aromatic moieties linked with flexible oligoethylene glycol moieties) using heat activation, i.e., a reaction temperature of 195° C. or 200° C. Uzawa et al. (1998) *Chem. Lett.* 4:307–308 describe a similar reaction wherein a thermally activated, Lewis acid-catalyzed, tandem Claisen reaction is used to prepare phenol-containing macrocyclic compounds. Synthesis of chiral crownophanes using a thermally activated tandem Claisen rearrangement reaction has been described as well; see Tokuhisa et al. (1999) *Tet. Lett.* 40:8007–8010. These tandem Claisen rearrangement reactions rely on thermal control and, consequently, are not suitable for synthesis of thermally unstable functional groups.

There is accordingly a need in the art for a tandem Claisen rearrangement reaction that proceeds quickly, can be carried out at or near room temperature, can be conducted as a "one-pot" synthesis, is activated using only catalytic quantities of a catalytic composition, and can be used to produce chiral products in enantiomerically pure form.

SUMMARY OF THE INVENTION

It is therefore a primary object of the invention to provide a novel tandem Claisen rearrangement reaction that addresses the above-mentioned need in the art.

It is another object of the invention to provide a method for preparing enantiomerically pure, chiral products via catalyzed Claisen rearrangement reactions that proceed in tandem.

It is still another object of the invention to provide a method for conducting two or more Claisen rearrangement reactions in tandem by reacting an appropriately substituted allylic compound with two or more equivalents of an acid chloride in the presence of a Lewis acid catalyst composition.

It is yet another object of the invention to provide a method for conducting Claisen rearrangement reactions in tandem by reacting an appropriately substituted allylic compound with a first acid chloride in the presence of a Lewis acid catalyst composition, and then reacting the product of the aforementioned reaction with a second acid chloride that may or may not be the same as the first.

It is a further object of the invention to provide such a method wherein the allylic compound is an allylic amine, an allylic ether, or an allylic thioether.

It is still a further object of the invention to provide such a method wherein one of the reactants or the catalyst composition is covalently linked, either directly or indirectly, to the surface of a solid support.

It is an additional object of the invention to provide such a method wherein the position and/or size of substituents on the allylic reactant determines the stereochemistry of the tandem reaction and the reaction product.

Additional objects, advantages and novel features of the invention will be set forth in part in the description which follows, and in part will become apparent to those skilled in the art upon examination of the following, or may be learned by practice of the invention.

In one embodiment, then, the invention provides a method for conducting two or more Claisen rearrangement reactions in tandem via Lewis acid catalysis. The method involves reaction of a total of N equivalents of an acid chloride with an allylic reactant (typically an allylic amine, an allylic thioether, or an allylic ether) in the presence of a Lewis acid catalyst composition, wherein N is the number of Claisen rearrangement reactions to proceed in tandem. The Lewis acid catalyst composition is comprised of two catalyst components, a first component composed of a Lewis acid, and a second component composed of a base, either a tertiary amine or a non-nitrogenous base. The allylic reactant is appropriately substituted so as to allow for two or more successive Claisen rearrangement reactions, each successive Claisen rearrangement utilizing the same or different acid chloride. The reaction is conducted under inert, nonaqueous conditions at a temperature typically in the range of approximately −110° C. to 200° C., and can give rise to a nonracemic, chiral product.

DETAILED DESCRIPTION OF THE INVENTION

It is to be understood that unless otherwise indicated this invention is not limited to specific reactants, catalyst compositions, or synthetic methods. It is also to be understood that the terminology used herein is for the purpose of describing particular embodiments only, and is not intended to be limiting.

As used in this specification and the appended claims, the singular forms "a," "an" and "the" include plural referents unless the context clearly dictates otherwise. Thus, reference to reference to "a Lewis acid" includes mixtures of Lewis acids, "a catalyst composition" includes mixtures of catalyst compositions, and the like.

In describing and claiming the present invention, the following terminology will be used in accordance with the definitions set out below.

The following definitions pertain to chemical structures, molecular segments and substituents:

As used herein, the phrase "having the structure" is not intended to be limiting and is used in the same way that the term "comprising" is commonly used. The tern "independently selected from the group consisting of" is used herein to indicate that the recited elements, e.g., R groups or the like, can be identical or different.

"Optional" or "optionally" means that the subsequently described event or circumstance may or may not occur, and that the description includes instances where said event or circumstance occurs and instances where it does not. For example, the phrase "optionally substituted hydrocarbyl" means that a hydrocarbyl moiety may or may not be substituted and that the description includes both unsubstituted hydrocarbyl and hydrocarbyl where there is substitution.

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of one to six carbon atoms, preferably one to four carbon atoms. "Substituted alkyl" refers to alkyl substituted with one or more substituent groups, and the terms "heteroatom-containing alkyl" and "heteroalkyl" refer to alkyl in which at least one carbon atom is replaced with a heteroatom.

The term "alkenyl" as used herein refers to a branched or unbranched hydrocarbon group typically although not necessarily containing 2 to about 24 carbon atoms and at least one double bond, such as ethenyl, n-propenyl, isopropenyl; s-propenyl, 2-propenyl, n-butenyl, isobutenyl, octenyl, decenyl, and the like. Generally, although again not necessarily, alkenyl groups herein contain 2 to about 12 carbon atoms. The term "lower alkenyl" intends an alkenyl group of two to six carbon atoms, preferably two to four carbon atoms. "Substituted alkenyt" refers to alkenyl substituted with one or more substituent groups, and the terms "heteroatom-containing alkenyl" and "heteroalkenyl" refer to alkenyl in which at least one carbon atom is replaced with a heteroatom.

The term "alkynyl" as used herein refers to a branched or unbranched hydrocarbon group typically although not necessarily containing 2 to about 24 carbon atoms and at least one triple bond, such as ethynyl, n-propynyl, n-butynyl, octynyl, decynyl, and the like. Generally, although again not necessarily, alkynyl groups herein contain 2 to about 12 carbon atoms. The term "lower alkynyl" intends an alkynyl group of two to six carbon atoms, preferably 2, 3 or 4 carbon atoms. "Substituted alkynyl" refers to alkynyl substituted with one or more substituent groups, and the terms "heteroatom-containing alkynyl" and "heteroalkynyl" refer to alkynyl in which at least one carbon atom is replaced with a heteroatom.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing one to six, more preferably one to four, carbon atoms.

Similarly, the term "alkyl thio" as used herein intends an alkyl group bound through a single, terminal thioether linkage; that is, an "alkyl thio" group may be represented as —S-alkyl where alkyl is as defined above. A "lower alkyl thio" group intends an alkyl thio group containing one to six, more preferably one to four, carbon atoms.

The term "allenyl" is used herein in the conventional sense to refer to a molecular segment having the structure —CH=C=CH$_2$. An "allenyl" group may be unsubstituted or substituted with one or more non-hydrogen substituents.

The term "aryl" as used herein, and unless otherwise specified, refers to an aromatic substituent containing a single aromatic ring or multiple aromatic rings that are fused together, linked covalently, or linked to a common group such as a methylene or ethylene moiety. The common linking group may also be a carbonyl as in benzophenone, an oxygen atom as in diphenylether, or a nitrogen atom as in diphenylamine. Preferred aryl groups contain one aromatic ring or two fused or linked aromatic rings, e.g., phenyl, naphthyl, biphenyl, diphenylether, diphenylamine, benzophenone, and the like. In particular embodiments, aryl substituents have 1 to about 200 carbon atoms, typically 1 to about 50 carbon atoms, and preferably 1 to about 20 carbon atoms. "Substituted aryl" refers to an aryl moiety substituted with one or more substituent groups, and the terms "heteroatom-containing aryl" and "heteroaryl" refer to aryl in which at least one carbon atom is replaced with a heteroatom.

The term "aralkyl" refers to an alkyl group with an aryl substituent, and the term "aralkylene" refers to an alkylene group with an aryl substituent; the term "alkaryl" refers to an aryl group that has an alkyl substituent, and the term "alkarylene" refers to an arylene group with an alkyl substituent.

The terms "halo" and "halogen" are used in the conventional sense to refer to a chloro, bromo, fluoro or iodo substituent. The terms "haloalkyl," "haloalkenyl" or "haloalkynyl" (or "halogenated alkyl," "halogenated alkenyl," "halogenated aromatic" or "halogenated alkynyl") refers to an alkyl, alkenyl, aromatic or alkynyl group, respectively, in which at least one of the hydrogen atoms in the group has been replaced with a halogen atom.

The term "heteroatom-containing" as in a "heteroatom-containing hydrocarbyl group" refers to a molecule or molecular fragment in which one or more carbon atoms is replaced with an atom other than carbon, e.g., nitrogen, oxygen, sulfur, phosphorus or silicon. Similarly, the term "heteroalkyl" refers to an alkyl substituent that is heteroatom-containing, the term "heterocyclic" refers to a cyclic substituent that is heteroatom-containing, the term "heteroaryl" refers to an aryl substituent that is heteroatom-containing, and the like. When the term "heteroatom-containing" appears prior to a list of possible heteroatom-containing groups, it is intended that the term apply to every member of that group. That is, the phrase "heteroatom-containing alkyl, alkenyl and alkynyl" is to be interpreted as "heteroatom-containing alkyl, heteroatom-containing alkenyl and heteroatom-containing alkynyl."

"Hydrocarbyl" refers to univalent hydrocarbyl radicals containing 1 to about 30 carbon atoms, preferably 1 to about 24 carbon atoms, most preferably 1 to about 12 carbon atoms, including branched or unbranched, saturated or unsaturated species, such as alkyl groups, alkenyl groups, aryl groups, and the like. The term "lower hydrocarbyl" intends a hydrocarbyl group of one to six carbon atoms, preferably one to four carbon atoms. The term "hydrocarbylene" intends a divalent hydrocarbyl moiety containing 1 to about 30 carbon atoms, preferably 1 to about 24 carbon atoms, most preferably 1 to about 12 carbon atoms, including branched or unbranched, saturated or unsaturated species, or the like. The term "lower hydrocarbylene" intends a hydrocarbylene group of one to six carbon atoms, preferably one to four carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom.

A "Lewis acid" refers to any species with a vacant orbital, in contrast to a "Lewis base," which refers to a compound with an available pair of electrons, either unshared or in a π-orbital. Typically, a Lewis acid refers to a compound containing an element that is two electrons short of having a complete valence shell.

By "substituted" as in "substituted hydrocarbyl," "substituted hydrocarbylene," "substituted alkyl," "substituted alkenyl" and the like, as alluded to in some of the aforementioned definitions, is meant that in the hydrocarbyl, hydrocarbylene, alkyl, alkenyl or other moiety, at least one hydrogen atom bound to a carbon atom is replaced with one or more substituents that are functional groups such as hydroxyl, alkoxy, thio, amino, halo, silyl, and the like. When the term "substituted" appears prior to a list of possible substituted groups, it is intended that the term apply to every member of that group. That is, the phrase "substituted alkyl, alkenyl and alkynyl" is to be interpreted as "substituted alkyl, substituted alkenyl and substituted alkynyl." Similarly, "optionally substituted alkyl, alkenyl and alkynyl" is to be interpreted as "optionally substituted alkyl, optionally substituted alkenyl and optionally substituted alkynyl."

The term "amino" is used herein to refer to the —NH$_2$ group, while "substituted amino" refers to —NZ$^1$Z$^2$ groups, where each of Z$^1$ and Z$^2$ is independently selected from the group consisting of optionally substituted hydrocarbyl and heteroatom-containing hydrocarbyl, or wherein Z$^1$ and Z$^2$ are linked to form an optionally substituted hydrocarbylene or heteroatom-containing hydrocarbylene bridge.

The term "sulihydryl" is used herein to refer to the —SH group, while "thio" is used herein to refer to the group —SZ$^1$, where Z$^1$ is selected from the group consisting of optionally substituted hydrocarbyl and hetero-containing hydrocarbyl. A compound containing a sulfur atom bound to two Z$^1$ moieties is termed a "thioether."

The term "chiral" refers to a structure that does not have an improper rotation axis (S$_n$), i.e., it belongs to point group C$_n$ or D$_n$. Such molecules are thus chiral with respect to an axis, plane or center of asymmetry. Preferred "chiral" molecules herein are in enantiomerically pure form, such that a particular chiral molecule represents at least about 95 wt. % of the composition in which it is contained, more preferably at least about 99 wt. % of that composition.

The term "enantioselective" refers to a chemical reaction that preferentially results in one enantiomer relative to a second enantiomer, i.e., gives rise to a product in which one enantiomer represents at least about 51 wt. % of the product. Preferably, in the enantioselective reactions herein, the selectively favored enantiomer represents at least about 85 wt. % of the product, optimally at least about 95 wt. % of the product.

As used herein all reference to the elements and groups of the Periodic. Table of the Elements is to the version of the table published by the Handbook of Chemistry and Physics, CRC Press, 1995, which sets forth the new IUPAC system for numbering groups. In the chemical structures herein, the use of bold and dashed lines to denote particular conformation of groups again follows APACE convention. The symbols "α" and "β" indicate the specific stereochemical configuration of a substituent at an asymmetric carbon atom in a chemical structure as drawn. Thus "β" denoted by a broken line, indicates that the group in question is below the general plane of the molecule as drawn, and "α," denoted by a bold line, indicates that the group in question is above the general plane of the molecule as drawn. The bond symbol

refers to a covalent bond that may be either α or β.

In one embodiment, then, the invention provides a method for conducting a tandem Claisen rearrangement reaction, comprising reacting an allylic reactant with an acid chloride in the presence of a Lewis acid catalyst composition comprising a first catalyst component composed of a Lewis acid, and a second catalyst component composed of a base, either a tertiary amine or a non-nitrogenous base, wherein the allylic reactant is substituted with at least two functional groups that enable the reactant to undergo at least two successive Claisen rearrangement reactions. The reaction is conducted under inert, nonaqueous conditions at a temperature typically in the range of approximately –110° C. to 200° C., and can give rise to a nonracemic, chiral product. As will be explained in further detail, the stereochemistry of the reaction product is readily controlled by the stereochemistry of the allylic reactant.

The two-step reaction wherein an allylic reactant is substituted with two functional groups that enable the reactant to undergo two successive Claisen rearrangement reactions proceeds according to schemes 1 and 2. The first of the two Claisen reactions is represented in Scheme 1, while the second is shown in Scheme 2:

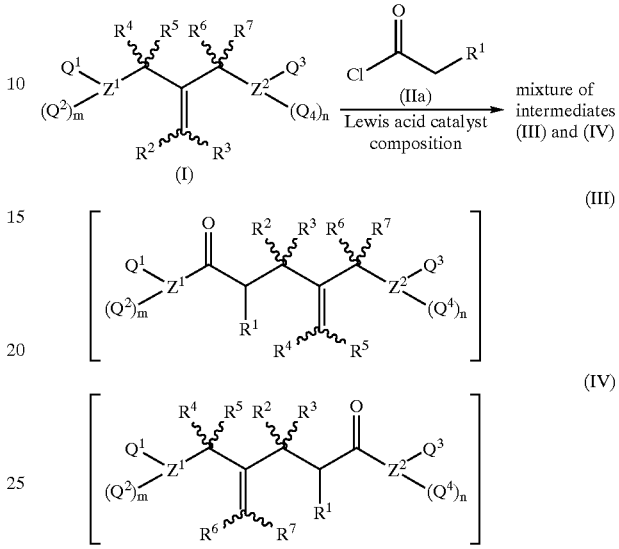

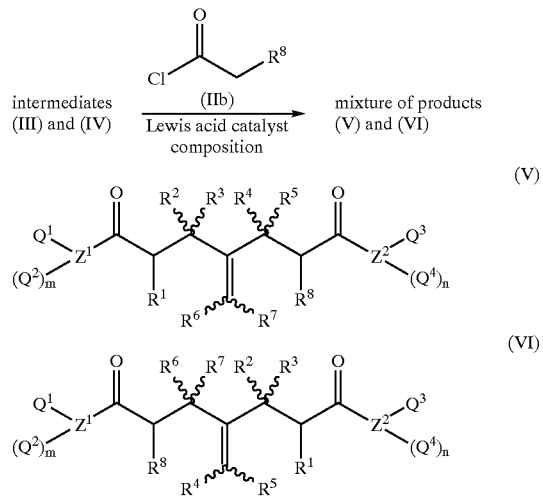

While not wishing to be bound by theory, it is proposed that the allylic reactant (I) and intermediates (III) and (IV) act to convert the acid chlorides (IIa) and (IIb) to ketene intermediates R$^1$=C=O and R$^8$=C=O respectively, which then undergo a further Claisen rearrangement reaction with the allylic reactant in Scheme 1 or the allylic intermediates (III) and (IV) in Scheme 2. In compounds (I), (IIa), (IIb), (III), (IV) and (V), the various substituents are as follows:

R$^1$, R$^2$, R$^3$, R$^4$, R$^5$, R$^6$, R$^7$ and R$^8$ are independently selected from the group consisting of hydrido, halo, hydroxyl, sulfhydryl, amino, substituted amino, hydrocarbyl (e.g., alkyl, alkenyl, alkynyl, aryl, alkaryl, aralkyl, etc.), substituted hydrocarbyl (e.g., substituted alkyl, alkenyl, alkynyl, aryl, alkaryl, aralkyl, etc.), heteroatom-containing hydrocarbyl (e.g., heteroatom-containing alkyl, alkenyl, alkynyl, aryl, alkaryl, aralkyl, etc.), and substituted heteroatom-containing hydrocarbyl (e.g., substituted heteroatom-containing alkyl, alkenyl, alkynyl, aryl, alkaryl, aralkyl, etc.).

$Z^1$ and $Z^2$ are independently N, O or S.

The subscript "m" is zero or 1, with the proviso that when $Z^1$ is N, m is 1, and when $Z^1$ is O or S, m is zero. Similarly, n is zero or 1, with the proviso that when $Z^2$ is N, n is 1, and when $Z^2$ is S or O, n is zero.

$Q^1$, $Q^2$, $Q^3$ and $Q^4$ are independently selected from the group consisting of hydrocarbyl (e.g., alkyl, alkenyl, alkynyl, aryl, alkaryl, aralkyl, etc.), substituted hydrocarbyl (e.g., substituted alkyl, alkenyl, alkynyl, aryl, alkaryl, aralkyl, etc.), heteroatom-containing hydrocarbyl (e.g., heteroatom-containing alkyl, alkenyl, alkynyl, aryl, alkaryl, aralkyl, etc.), and substituted heteroatom-containing hydrocarbyl (e.g., substituted heteroatom-containing alkyl, alkenyl, alkynyl, aryl, alkaryl, aralkyl, etc.), or, when $Z^1$ is N and m is 1, $Q^1$ and $Q^2$ are joined together in a ring structure, generally a five- or six-membered cyclic group such as piperidinyl, piperazinyl, pyrrolidinyl, imidazolidinyl, morpholino, or the like, and similarly, when $Z^2$ is N and n is 1, $Q^3$ and $Q^4$ may be joined together in a ring structure such as a five- or six-membered cyclic group such as piperidinyl, piperazinyl, pyrrolidinyl, imidazolidinyl, morpholino, or the like.

When a reaction involving more than two successive Claisen rearrangements is desired, it will be appreciated that the allylic reactant (I) must then be substituted with at least one additional $-Z^aQ^x(Q^y)_m$, group, e.g., one or more of $R^4$, $R^5$, $R^6$ and $R^7$ may be $-Z^aQ^x(Q^y)_m$ wherein $Z^a$ is defined as for $Z^1$ and $Z^2$, i.e., $Z^a$ is N, O or S, and $Q^x$ and $Q^y$ are defined as for $Q^1$, $Q^2$, $Q^3$ and $Q^4$. It will also be appreciated that such reactions may also include additional disparate acid chloride reactants. Additional allylic functionalities may be present as well.

Preferably, allylic reactant (I) contains at least one allylic amine group, i.e., at least one of $Z^1$ and $Z^2$ is N. Most preferably, allylic reactant (I) is an allylic diamine, i.e., $Z^1$ and $Z^2$ are both N. Examples of preferred allylic reactants include, but are not limited to, the following:

4-[2-(morpholin-4-ylmethyl)prop-2-enyl]morpholine;
4-[(2E)-2-(morpholin-4-ylmethyl)but-2-enyl]morpholine;
4-[(2Z)-2-(morpholin-4-ylethyl)but-2-enyl]morpholine;
4-[(2E)-1-methyl-2-(1-methyl-1-morpholin-4-ylethyl)but-2-enyl]morpholine;
4-[(2E)-1,1,3-trimethyl-2-(1-methyl-1-morpholin4-ylethyl)pent-2-enyl]morpholine;
4-[(2Z)-1,1-dimethyl-2-(morpholin-4-ylphenylmethyl)but-2-enyl]morpholine;
4-[(2E)-2-(chloromorpholin-4-ylmethyl)-1,3-dimethylbut-2-enyl]morpholine;
4-[(2Z)-1-chloro-1,3-dimethyl-2-(morpholin-4-ylphenylmethyl)pent-2-enyl]morpholine;
4-[2-(piperidylmethyl)prop-2-enyl]morpholine;
4-[(2Z)-2-(piperidylmethyl)but-2-enyl]morpholine;
4-[(2Z)-1-methyl-2-(piperidylmethyl)but-2-enyl]morpholine;
4-[(2E)-1,1-dimethyl-2-(piperidylethyl)but-2-enyl]morpholine;
4-[(2Z)-1,1,3-trimethyl-2-(1-methyl-1-piperidylethyl)pent-2-enyl]morpholine;
4-[(2Z)-1,1-dimethyl-2-(phenylpiperidylmethyl)but-2-enyl]morpholine;
4-[(2E)-2-(chloropiperidylmethyl)-1,3-dimethylbut-2-enyl]morpholine;
4-[(2Z)-1-chloro-1,3-dimethyl-2-(phenylpiperidylmethyl)pent-2-enyl]morholine;
4-[2-(piperazinylmethyl)prop-2-enyl]morpholine;
4-[(2Z)-2-(piperazinylmethyl)but-2-enyl]morpholine;
4-[(2Z)-1-methyl-2-(piperazinylmethyl)but-2-enyl]morpholine;
4-[(2E)-1,1-dimethyl-2-(piperazinylethyl)but-2-enyl]morpholine;
4-[(2Z)-1,1,3-trimethyl-2-(1-methyl-1-piperazinylethyl)pent-2-enyl]morpholine;
4-[(2Z)-1,1-dimethyl-2-(phenylpiperazinylmethyl)but-2-enyl]morpholine;
4-[(2E)-2-(chloropiperazinylmethyl)-1,3-dimethylbut-2-enyl]morpholine;
4-[(2Z)-1-chloro-1,3-dimethyl-2-(phenylpiperazinylmethyl)pent-2-enyl]morpholine;
4-[2-(pyrroidinylmethyl)prop-2-enyl]morpholine;
4-[(2Z)-2-(pyrrolidinylmethyl)but-2-enyl]morpholine;
4-[(2Z)-1-methy-2-(pyrrolidinylmethyl)but-2-enyl]morpholine;
4-[(2E)-1,1-dimethyl-2-(pyrrolidinylethyl)but-2-enyl]morpholine;
4-[(2Z)-1,1,3-trimethyl-2-(1-methyl-1-pyrrolidinylethyl)pent-2-enyl]morpholine;
4-[(2Z)-1,1-dimethyl-2-(phenylpyrrolidinylmethyl)but-2-enyl]morpholine;
4-[(2E)-2-(chloropyrrolidinylmethyl)-1,3-dimethylbut-2-enyl]morpholine;
4-[(2Z)-1-chloro-1,3-dimethyl-2-(phenylpyrrolidinylmethyl)pent-2-enyl]morpholine;
4-[2-(imidazolidinylmethyl)prop-2-enyl]morpholine;
4-[(2E)-2-(imidazolidinylmethyl)but-2-enyl]morpholine;
4-[(2Z)-2-(imidazolidinylmethyl)-1-methylbut-2-enyl]morpholine;
4-[(2E)-2-(imidazolidinylethyl)-1,1-dimethylbut-2-enyl]morpholine;
4-[(2E)-2-(1-imidazolidinyl-isopropyl)-1,1,3-trimethylpent-2-enyl]morpholine;
4-[(2Z)-2-(imidazolidinyiphenylmethyl)-1,1,1-dimethylbut-2-enyl]morpholine;
4-[(2Z)-1-chloro-2-(imidazolidinylphenylmethyl)-1,3-dimethylpent-2-enyl]morpholine;
4-(2-azidomethyl-allyl)-morpholine;
4-(2-azidomethyl-but-2-enyl)-morpholine;
4-(3-azidomethyl-pent-3-enyl)-morpholine;
4-(2-azidomethyl-1,1-dimethyl-but-2-enyl)-morpholine;
4-(2-azidomethyl-1,1,3-trimethyl-pent-2-enyl)-morpholine;
4-[2-(azido-phenyl-methyl)-1,1-dimethyl-but-2-enyl]-morpholine;
4-[2-(azido-chloro-methyl)-1,3-dimethyl-but-2-enyl]-morpholine;
4-[2-(azido-phenyl-methyl)-1-chloro-1,3-dimethyl-pent-2-enyl]-morpholine;
[2-(piperidylmethyl)prop-2-enyl]piperidine;
[(2E)-2-(piperidylmethyl)but-2-enyl]piperidine;
[(2Z)-2-(piperidylethyl)but-2-enyl]piperidine;
[(2E)-1-methyl-2-(1-methyl-1-piperidylethyl)but-2-enyl]piperidine;
[(2E)-1,1,3-trimethyl-2-(1-methyl-1-piperidylethyl)pent-2-enyl]piperidine;
[(2Z)-1,3I-dimethyl-2-(phenylpiperidylmethyl)but-2-enyl]piperidine;
[(2E)-2-(chloropiperidylmethyl)-1,3-dimethylbut-2-enyl]piperidine;
[(2Z)-1-chloro-1,3-dimethyl-2-(phenylpiperidylmethyl)pent-2-enyl]piperidine;
[2-(piperidylmethyl)prop-2-enyl]piperazine;
[(2E)-2-(piperidylmethyl)but-2-enyl]piperazine;
[(2Z)-2-(piperidylethyl)but-2-enyl]piperazine;

[(2E)-1-methyl-2-(1-methyl-1-piperidylethyl)but-2-enyl]
piperazine;
[(2E)-1,1,3-trimethyl-2-(1-methyl-1-piperidylethyl)pent-2-
enyl]piperazine;
[(2Z)-2-(1-methyl-1-piperidylethyl)-1-phenylbut-2-enyl]
piperazine;
[(2E)-1-chloro-3-methyl-2-(piperidylethyl)but-2-enyl]
piperazine;
[(2Z)-2-(1-chloro-1-piperidylethyl)-3-methyl-1-phenylpent-
2-enyl]piperazine;
[2-(pyrrolidinylmethyl)prop-2-enyl]piperidine;
[(2E)-2-(pyrrolidinylmethyl)but-2-enyl]piperidine;
[(2Z)-1-methyl-2-(pyrrolidinylmethyl)but-2-enyl]
piperidine;
[(2E)-1,1-dimethyl-2-(pyrrolidinylethyl)but-2-enyl]
piperidine;
[(2E)-1,1,3-trimethyl-2-(1-methyl-1-pyrrolidinylethyl)pent-
2-enyl]piperidine;
[(2Z)-1,1-dimethyl-2-(phenylpyrrolidinylmethyl)but-2-
enyl]piperidine;
[(2E)-2-(chloropyrrolidinylmethyl)-1,3-dimethylbut-2-
enyl]piperidine;
[(2Z)-1-chloro-1,3-dimethyl-2-(phenylpyrrolidinylmethyl)
pent-2-enyl]piperidine;
[2-(piperidylmethyl)prop-2-enyl]imidazolidine;
[(2E)-2-(piperidylmethyl)but-2-enyl]imidazolidine;
[(2Z)-2-(piperidylethyl)but-2-enyl]imidazolidine;
[(2E)-1-methyl-2-(1-methyl-1-piperidyletmyl)but-2-enyl]
imidazolidine;
[(2E)-1,1,3-trimethyl-2-(1-methyl-1-piperidylethyl)pent-2-
enyl] imidazolidine;
[(2Z)-2-(1-methyl-1-piperidylethyl)-1-phenylbut-2-enyl]
imidazolidine;
[(2E)-1-chloro-3-methyl-2-piperidylethyl)but-2-enyl]
imidazolidine;
[(2Z)-2-(1-chloro-1-piperidylethyl)-3-methyl-1-phenylpent-
2-enyl]imidazolidine;
1-(2-azidomethyl-allyl)-piperidine;
1-(2-azidomethyl-but-2-enyl)-piperidine;
1-(3-azidomethyl-pent-3-enyl)-piperidine;
1-(2-azidomethyl-1,1-dimethyl-but-2-enyl)-piperidine;
1-(2-azidomethyl-1,1,3-trimethyl-bent-2-enyl)-piperidine;
1-[2-(azido-phenyl-methyl)-1-dimethyl-but-2-enyl]-
piperidine;
1-[2-(azido-chloro-methyl)-1,3-dimethyl-but-2-enyl]-
piperidine;
1-[2-(azido-phenyl-methyl)-1-chloro-1,3-dimethyl-pent-2-
enyl]-piperidine;
[2-(piperazinylmethyl)prop-2-enyl]piperazine;
[(2E)-2-(piperazinylmethyl)but-2-enyl]piperazine;
[(2Z)-2-(piperazinylethyl)but-2-enyl]piperazine;
[(2E)-1-methyl-2-(1-methyl-1-piperazinylethyl)but-2-enyl]
piperazine;
[(2E)-1,1,3-trimethyl-2-(1-methyl-1-piperazinylethyl)pent-
2-enyl]piperazine;
[(2Z)-1,1-dimethyl-2-(phenylpiperazinylmethyl)but-2-enyl]
piperazine;
[(2E)-2-(chloropiperazinylmethyl)-1,3-dimethylbut-2-enyl]
piperazine;
[(2Z)-1-chloro-1,3-dimethyl-2-(phenylpiperazinylmethyl)
pent-2-enyl]piperazine;
[2-pyrrolidinylmethyl)prop-2-enyl]piperazine;
[(2Z)-2-(pyrrolidinylmethyl)but-2-enyl]piperazine;
[(2Z)-1-methyl-2-(pyrrolidinylmethyl)but-2-enyl]
piperazine;
[(2E)-1,1-dimethyl-2-(pyrrolidinylethyl)but-2-enyl]
piperazine;

[(2Z)-1,1,3-trimethyl-2-(1-methyl-1-pyrrolidinylethyl)pent-
2-enyl]piperazine;
[(2Z)-1,1-dimethyl-2-(phenylpyrrolidinylmethyl)but-2-
enyl]piperazine;
[(2E)-2-(chloropyrrolidinylmethyl)-1,3-dimethylbut-2-
enyl]piperazine;
[(2Z)-1-choro-1,3-dimethyl-2-(phenylpyrrolidinylmethyl)
pent-2-enyl]piperazine;
[2-(imidazolidinylmethyl)prop-2-enyl]piperazine;
[(2E)-2-(imidazolidinylmethyl)but-2-enyl]piperazine;
[(2Z)-2-(imidazolidinylmethyl)-1-methylbut-2-enyl]
piperazine;
[(2E)-2-(imidazolidinylethyl)-1,1-dimethylbut-2-enyl]
piperazine;
[(2E)-2-(1-imidazolidinyl-isopropyl)-1,1,3-trimethylpent-2-
enyl]piperazine;
[(2Z)-2-(imidazolidinylphenylmethyl)-1,1-dimethylbut-2-
enyl]piperazine;
[(2E)-2-(chloroimidazolidinylmethyl)-1,3-dimethylbut-2-
enyl]piperazine;
[(2Z)-1-chloro-2-(imidazolidinylphenylmethyl)-1,3-
dimethylpent-2-enyl]piperazine;
1-(2-azidomethyl-allyl)-piperazine;
1-(2-azidomethyl-but-2-enyl)-piperazine;
1-(3-azidomethyl-pent-3-enyl)-piperazine;
1-(2-azidomethyl-1,1-dimethyl-but-2-enyl)-piperazine;
1-(2-azidomethyl-1,1,3-trimethyl-pent-2-enyl)-piperazine;
1-[2-(azido-phenyl-methyl)-1,1-dimethyl-but-2-enyl]-
piperazine;
1-[2-(azido-chloro-methyl)-1,3-dimethyl-but-2-enyl]-
piperazine;
1-[2-(azido-phenyl-methyl)-1-chloro-1,3-dimethyl-pent-2-
enyl]-piperazine;
[2-(pyrrolidinylmethyl)prop-2-enyl]pyrrolidine;
[(2E)-2-(pyrrolidinylmethyl)but-2-enyl]pyrrolidine;
[(2Z)-2-(pyrrolidinylethyl)but-2-enyl]pyrrolidine;
[(2E)-1-methyl-2-(1-methyl-1-pyrrolidinylethyl)but-2-enyl]
pyrrolidine;
[(2E)-1,1,3-trimethyl-2-(1-methyl-1-pyrrolidinylethyl)pent-
2-enyl]pyrrolidine;
[(2Z)-1,1-dimethyl-2-(phenylpyrrolidinylmethyl)but-2-
enyl]pyrrolidine;
[(2E)-2-(chloropyrrolidinylmethyl)-1,3-dimethylbut-2-
enyl]pyrrolidine;
[(2Z)-1-chloro-1,3-dimethyl-2-(phenylpyrrolidinylmethyl)
pent-2-enyl]pyrrolidine;
[2-(pyrrolidinylmethyl)prop-2-enyl]imidazolidine;
[(2E)-2-pyrrolidinylmethyl)but-2-enyl]imidazolidine;
[(2Z)-2-(pyrrolidinylethyl)but-2-enyl]imidazolidine;
[(2E)-1-methyl-2-(1-methyl-1-pyrrolidinylethyl)but-2-enyl]
imidazolidine;
[(2E)-1,3-trimethyl-2-(1-methyl-1-pyrrolidinylethyl)pent-2-
enyl]imidazolidine;
[(2Z)-2-(1-methyl-1-pyrrolidinylethyl)-1-phenylbut-2-enyl]
imidazolidine;
[(2E)-1-chloro-3-methyl-2-(pyrrolidinylethyl)but-2-enyl]
imidazolidine;
[(2Z)-2-(1-chloro-1-pyrrolidinylethyl)-3-methyl-1-
phenylpent-2-enyl]imidazolidine;
1-(2-azidomethyl-allyl)-pyrrolidine;
1-(2-azidomethyl-but-2-enyl)-pyrrolidine;
1-(3-azidomethyl-pent-3-enyl)-pyrrolidine;
1-(2-azidomethyl-1,1-dimethyl-but-2-enyl)-pyrrolidine;
1-(2-azidomethyl-1,1,3-trimethyl-pent-2-enyl)-pyrrolidine;
1-[2-(azido-phenyl-methyl)-1,1-dimethyl-but-2-enyl]-
pyrrolidine;
1-[2-(azido-chloro-methyl)-1,3-dimethyl-but-2-enyl]-
pyrrolidine;

1-[2-(azido-phenyl-methyl)-1-chloro-1,3-dimethyl-pent-2-enyl]-pyrrolidine;
[2-(imidazolidinylmethyl)prop-2-enyl]imidazolidine;
[(2E)-2-(imidazolidinylmethyl)but-2-enyl]imidazolidine;
[(2Z)-2-(imidazolidinylethyl)but-2-enyl]imidazolidine;
[(2E)-2-(1-imidazolidinyl-isopropyl)-1-methylbut-2-enyl]imidazolidine;
[(2E)-2-(1-imidazolidinyl-isopropyl)-1,1,3-trimethylpent-2-enyl]imidazolidine;
[(2Z)-2-(imidazolidinylphenylmethyl)-1,1-dimethylbut-2-enyl]imidazolidine;
[(2E)-2-(chloroimidazolidinylmethyl)-1,3-dimethylbut-2-enyl]imidazolidine;
[(2Z)-1-chloro-2-(imidazolidinylphenylmethyl)-1,3-dimethylpent-2-enyl]imidazolidine;
2-(2-azidomethyl-allyl)-imidazolidine;
2-(2-azidomethyl-but-2-enyl)-imidazolidine;
2-(3-azidomethyl-pent-3-enyl)-imidazolidine;
2-(2-azidomethyl-1,1-dimethyl-but-2-enyl)-imidazolidine;
2-(2-azidomethyl-1,1,3-trimethyl-pent-2-enyl)-imidazolidine;
2-[2-(azido-phenyl-methyl)-1,1-dimethyl-but-2-enyl]-imidazolidine;
2-[2-(azido-chloro-methyl)-1,3-dimethyl-but-2-enyl]-imidazolidine;
2-[2-(azido-phenyl-methyl)-1-chloro-1,3-dimethyl-pent-2-enyl]-imidazolidine;
3-azido-2-azidomethyl-propene;
1-azido-2-azidomethyl-but-2-ene;
5-azido-3-azidomethyl-pent-2-ene;
4-azido-3-azidomethyl-4-methyl-pent-2-ene;
2-azido-3-azidomethyl-2,4-dimethyl-hex-3-ene;
(1,3-diazido-2-tert-butyl-allyl)-benzene;
4-azido-3-(azido-chloro-methyl)-2-methyl-pent-2-ene; and
[1-azido-2-(1-azido-1-chloro-ethyl)-3-methyl-pent-2-enyl]-benzene.

The acid chlorides (IIa) and (IIb) may be any acid chlorides that are suitable for undergoing the rearrangement reaction with the allylic reactant (I) as illustrated in Scheme 1. Acid chlorides (IIa) and (IIb) may be the same or different, i.e., $R^1$ and $R^8$ may be the same or different. $R^1$ and $R^8$, as noted earlier herein, are hydrido, halo, hydroxyl, sulfhydryl, amino, substituted amino, hydrocarbyl (e.g., alkyl, alkenyl, alkynyl, aryl, alkaryl, aralkyl, etc.), substituted hydrocarbyl (e.g., substituted alkyl, alkenyl, alkynyl, aryl, alkaryl, aralkyl, etc.), heteroatom-containing hydrocarbyl (e.g., heteroatom-containing alkyl, alkenyl, alkynyl, aryl, alkaryl, aralkyl, etc.), or substituted heteroatom-containing hydrocarbyl (e.g., substituted heteroatom-containing alkyl, alkenyl, alkynyl, aryl, alkaryl, aralkyl, etc.), and is preferably hydrocarbyl, substituted hydrocarbyl, heteroatom-containing hydrocarbyl, or substituted heteroatom-containing hydrocarbyl. Most preferably, $R^1$ and $R^8$ are alkyl (with lower alkyl substituents such as methyl being optimal), benzyloxy or thiophenyl.

Examples of suitable acid chlorides thus include, but are not limited to, propanoyl chloride, 2-methylpropanoyl chloride, 2-ethylpropanoyl chloride, 2-cyclohexylpropanoyl chloride, 2-phenylpropanoyl chloride, butanoyl chloride, 2-methylbutanoyl chloride, 2-ethylbutanoyl chloride, 2-cyclohexylbutanoyl chloride, 2-phenylbutanoyl chloride, 3-methylbutanoyl chloride, 3-ethylbutanoyl chloride, 3-cyclohexylbutanoyl chloride, 3-phenylbutanoyl chloride, 2-(phenylmethoxy)acetyl chloride, 2-(p-methylphenylmethoxy)-acetylchloride, 2-(p-ethylphenylmethoxy)acetylchloride, 2-(p-nitrophenylmethoxy)acetyl-chloride, 2-(o-methylphenylmethoxy)acetylchloride, 2-(o-ethylphenylmethoxy)acetylchloride, 2-(o-nitrophenylmethoxy)acetylchloride, 2-phenylthioacetyl chloride, 2-(o-ethylphenyl)thioacetyl chloride, 2-(m-methylphenylmethoxy)acetylchloride, 2-(o-ethylphenylmethoxy)acetylchloride, 2-(m-nitrophenylmethoxy)acetylchloride, 2-phenylthioacetyl chloride, 2-(p-ethylphenyl)thioacetyl chloride, 2-(-pethylphenyl)thioacetyl chloride, 2-(nitrophenyl)thioacetyl chloride, 2-(o-methylphenyl)thioacetyl chloride, 2-(o-ethylphenyl)thioacetyl chloride, 2-(o-nitrophenyl)thioacetyl chloride, 2-(m-methylphenyl)thioacetyl chloride, 2-(m-ethylphenyl)thioacetyl chloride, 2-(m-nitrophenyl) thioacetyl chloride, and the like.

The catalyst composition comprises two catalyst components, a first component composed of a Lewis acid, and a second component composed of a base, either a tertiary amine or a non-nitrogenous base. Suitable Lewis acids generally have the structural formula (VII)

$$M(X)_a(Y)_b \qquad\qquad (VII)$$

wherein M is a metal, X is halide or halide-containing (e.g., $SbF_6^-$, $BF_4^-$), or is lower alkoxy, fluorinated lower alkoxy (e.g., $OCF_3$, $OCF_2CF_3$, $OCH_2CF_3$), sulfate, acetate, trifluoroacetate, or triflate (i.e., trifluoromethylsulfonate, or $-OSO_2CF_3$), Y is hydrocarbyl, substituted hydrocarbyl, heteroatom-containing hydrocarbyl, substituted heteroatom-containing hydrocarbyl, or an oxygen-containing or nitrogen-containing organic ligand, a is an integer of 1 or more, and the sum of a and b is in the range of 2 to $n_{max}$, where $n_{max}$ is the number of atoms that can bind to M through single covalent or coordination bonds. However, if Y is a bidentate (or multidentate) ligand, obviously it will be the sum of a and 2b (or xb, where x is the number of covalent or coordination bonds linking Y to M) that is in the range of 2 to $n_{max}$. For example, for titanium (M) having two chloro (X) substituents, a single bidentate ligand Y or two monodentate ligands Y may be present, insofar as $n_{max}$ for titanium is 4, and a, by virtue of the two chloro substituents, is 2. Thus, in the foregoing example, for a monodentate ligand Y, b will be (2 to $n_{max}$)—a, i.e., zero to 2, while for a bidentate ligand Y, b will be ½ ((2 to $n_{max}$)—a, i.e., zero or 1.

The metal M may be any metal in the Periodic Table of the Elements. Preferably, the metal is selected from the group consisting of Groups 2 through 13 of the Periodic Table of the Elements and the lanthanides. More preferred metals are Ti, Mg, Al, Sc, Y, Ni, Cu, Zn and Yb, and most preferred metals are Ti, Mg and Al.

Preferred X moieties are halide and triflate. Thus, X may be chloro, bromo, fluoro or iodo, but is typically chloro or bromo, and most preferably is chloro. Y may be, for example, alkyl, particularly lower alkyl (e.g., methyl, ethyl, n-propyl, isopropyl, n-butyl, s-butyl, t-butyl, etc.), aryl (e.g., phenyl, benzyl), aryloxy (e.g., benzyloxy), or the like, or may be a nitrogen-containing or oxygen-containing organic ligand. One example of a suitable oxygen-containing organic ligand is tetrakis-3,5-bis(trifluoromethyl)-phenylborate, commonly referred to as "BARF." Exemplary nitrogen-containing ligands are unsaturated nitrogen-containing ligands such as (VIIIa) and (VIIIb)

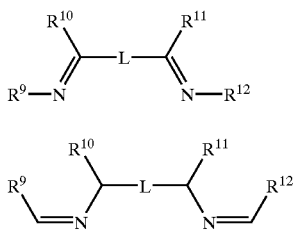

(VIIIa)

(VIIIb)

wherein L is a hydrocarbylene, substituted hydrocarbylene, heteroatom-containing hydrocarbylene, substituted heteroatom-containing hydrocarbylene or heteroatom linkage, $R^9$, $R^{10}$, $R^{11}$ and $R^{12}$ are as defined for $R^1$ through $R^6$, and wherein $R^9$ and $R^{10}$ and/or $R^{11}$ and $R^{12}$ may be linked to form a hydrocarbylene, substituted hydrocarbylene, heteroatom-containing hydrocarbylene, or substituted heteroatom-containing hydrocarbylene bridge. Preferred subsets of such ligands have the structure (IXa) and (IXb)

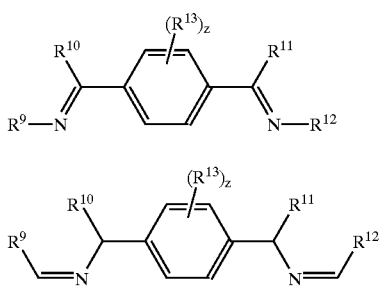

(IXa)

(IXb)

wherein $R^{13}$ is as defined for $R^9$, $R^{10}$ and $R^{12}$, and z is an integer in the range of zero to 5 inclusive. Such ligands include, for example, those having the structural formula (X), wherein $R^{14}$, $R^{15}$, $R^{16}$ and $R^{17}$ are defined as for $R^{13}$, with one specific such ligand, 4-[2-(3,4-dichlorophenyl)(1,3-oxazolin-4-yl)]-1-methoxybenzene, shown in structural formula (XI)

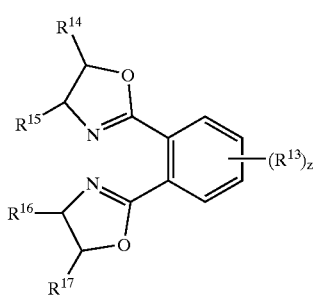

(XI)

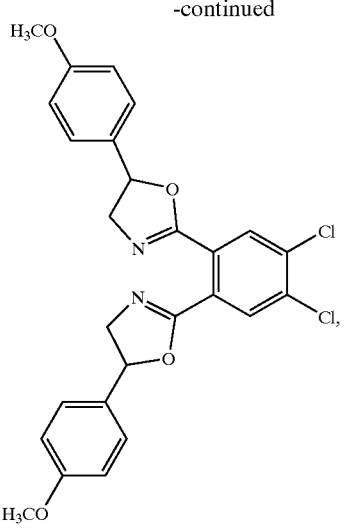

in which case a corresponding titanium catalyst component might have the structural formula (XII)

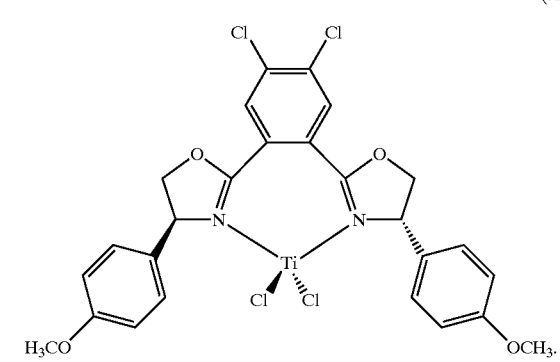

(XII)

The second component of the catalyst composition is a base, either a tertiary amine or a non-nitrogenous base. Tertiary amines will have the structure $NR^{18}R^{19}R^{20}$ wherein $R^{18}$, $R^{19}$ and $R^{20}$ are independently hydrocarbyl, substituted hydrocarbyl, heteroatom-containing hydrocarbyl or substituted heteroatom-containing hydrocarbyl, or wherein two of $R^{18}$, $R^{19}$ and $R^{20}$ are linked to form a hydrocarbylene, substituted hydrocarbylene, heteroatom-containing hydrocarbylene or substituted heteroatom-containing hydrocarbylene bridge. Preferred $R^{18}$, $R^{19}$ and $R^{20}$ substituents are alkyl, e.g., lower alkyl. Other useful tertiary amines are nitrogen-containing heterocycles in which at least one nitrogen heteroatom is in the form —N=, as in, for example, pyridine. Examples of tertiary amines suitable as the second catalyst component thus include, but are not limited to, trimethylamine, triethylamine, methyldiethylamine, ethyldimethylamine, methyldiisopropylamine, dimethylisopropylamine, ethyldiisopropylamine, diethylisopropylamine, N-methylpyrrolidine, N-vinylpyrrolidine, N-methylpyridazine, N-methylmorpholine, pyridine, 4-dimethylaminopyridine, 2,6-di-t-butyl-4-methylpyridine, N-methylimidazole, etc.

Non-nitrogenous bases that may serve as the second component of the catalyst composition include, without limitation, inorganic hydroxides, inorganic oxides, and metal carbonates. Inorganic hydroxides include, for example, ammonium hydroxide, alkali metal hydroxide and alkaline earth metal hydroxides, such as sodium hydroxide, calcium hydroxide, potassium hydroxide, magnesium hydroxide, and the like. Inorganic oxides include, for example, magnesium oxide, calcium oxide, and the like. Metal carbonates include sodium carbonate and potassium carbonate. Preferred non-nitrogenous bases are metal hydroxides such as sodium and potassium hydroxide and metal carbonates such as sodium and potassium carbonate.

Procedurally, the reaction is carried out as follows when a single acid chloride is used. The Lewis acid component (VII) of the catalyst composition is combined with the allylic reactant (I) in a suitable solvent, e.g., an aliphatic hydrocarbon, an aromatic hydrocarbon, a halohydrocarbon, an ether, a cyclic ether, or the like. Suitable hydrocarbon solvents include isobutane, butane, pentane, hexane, octane, cyclohexane, methylcyclohexane, benzene, toluene, and the like. Preferred solvents are polar organic solvents, including halohydrocarbons, ethers, and the like, and particularly preferred solvents include such methylene chloride, tetrahydrofuran, diethylether, dimethylether, diisopropylether, dimethoxymethane, dioxane, acetone, methyl ethyl ketone, isobutyl methyl ketone, dimethylformamide, dimethylacetamide, N-methylpyrrolidone, acetonitrile and chloroform. Methylene chloride is most preferred. Solvents may be used alone or in combination.

The tertiary amine or non-nitrogenous base component of the catalyst composition is then added to the reaction mixture, followed by addition of approximately N equivalents of the acid chloride (IIa) wherein N is the number of successive Claisen rearrangement reactions that are desired (note that N is also the number of functional groups on the allylic reactant that enable the reactant to undergo Claisen rearrangement). Preferably, although not necessarily, N is 2. The reaction is continued until the acid chloride is consumed. Consumption of the acid chloride may be determined using, for example, thin layer chromatography. Generally, the reaction is complete within about 2 to 48 hours, typically within about 2 to 6 hours. After completion, the product is recovered using any suitable means known to those skilled in the art. The recovery process can include separation of by-products, if any, and evaporation of the solvent. The product may be recovered, for example, by extraction, recrystallization, filtration, or other purification processes known in the art.

When two or more different acid chlorides are used, the reaction is carried out by combining the Lewis acid component (VII) with the allylic reactant in a suitable solvent as described above, followed by addition of the tertiary amine or non-nitrogenous base component of the catalyst composition and one equivalent of a first acid chloride, i.e., an acid chloride having the structure (IIa). This results in a single Claisen rearrangement reaction and intermediates (III) and (IV). Then, a second acid chloride is added, i.e., an acid chloride having the structure (IIb). A second rearrangement reaction results in products (V) and (VI). Additional acid chlorides may be added when the allylic reactant (I) is substituted with additional —$Z^aQ^x(Q^y)_m$ groups, resulting in additional Claisen rearrangement reactions. Alternatively, the allylic reactant (I) may be combined with two or more acid chlorides simultaneously.

The catalytic reaction is preferably although not necessarily homogeneous, and may be carried out in batch, semi-continuously or continuously, under inert, nonaqueous conditions (e.g., under an atmosphere of dry nitrogen and in an organic, completely nonaqueous solvent), at autogenous pressure or higher, depending, for example, on the nature of the catalyst composition and reactants used. The reaction temperature will generally be in the range of about –100° C. to 200° C., preferably in the range of about –78° C. to 100° C., most preferably in the range of about 0° C. to 50° C.; the reaction may be conveniently carried out at room temperature. The amount of total catalyst composition—i.e., the total of the Lewis acid component and the tertiary amine or non-nitrogenous base component—is generally in the range of 5 mole % to 300 mole % relative to the allylic reactant (I), the molar ratio of the Lewis acid component to the base component in the catalyst composition is generally in the range of about 1:2 to 2:1, preferably in the range of about 1.25:1 to 1:1.25, and the molar ratio of the reactants, i.e., the molar ratio of the allylic reactant (I) to the acid chloride (II), is typically in the range of about 1:10 to 10:1, preferably in the range of about 1:2 to 2:1, and most preferably is about 1:1.

The novel Claisen rearrangement reaction can also be carried out on a solid support, using solid phase synthesis techniques. Solid-phase synthesis enables use of the reaction in combinatorial chemistry processes, wherein an array or "matrix" of reactions are conducted in parallel on a single substrate. In this embodiment, the allylic reactant (I), the acid chloride (II), or the catalyst is bound either directly or indirectly to the surface of a solid substrate, if indirectly, through a cleavable or noncleavable linker. For example, the allylic reactant (I) can be linked to the surface of a substrate through $R^6$, $Q^1$, $Q^2$, or the like, and the acid chloride (II) can be linked to the surface of a substrate through the methylene group linking $R^1$ to the carbonyl moiety. Any solid support may be used. Typical substrates are those conventionally used in solid phase chemistry and which allow for chemical synthesis thereon. The only limitation upon the materials useful for constructing substrates is that they must be compatible with the reaction conditions to which they are exposed. Suitable substrates useful in practicing the methods of the invention include, but are not limited to, organic and inorganic polymers (e.g., polyethylene, polypropylene, polystyrene, polytetrafluoroethylene), metal oxides (e.g., silica, alumina), mixed metal oxides, metal halides (e.g., magnesium chloride), minerals, quartz, zeolites, and the like. Other substrate materials will be apparent to those of skill in the art.

The present invention thus represents an important contribution to the field of synthetic organic chemistry by providing an entirely new method for conducting Claisen rearrangement reactions using Lewis acid catalysis and at least one acid chloride as a reactant. The present process is useful in conjunction with an enormous variety of reactants and Lewis acid catalyst compositions, and, importantly, can be carried out at room temperature using a "one-pot" synthesis to prepare chiral compounds in enantiomerically pure form having a specific and predetermined stereochemistry. That is, such reaction products are "chiral" compounds. The stereochemistry of the product, i.e., the positioning of $R^2$, $R^3$, $R^4$, $R^5$, $R^6$ and $R^7$ in the reaction products (V) and (VI)

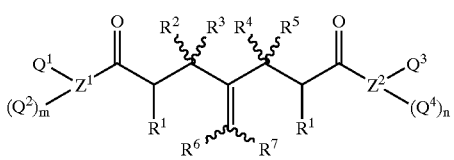
(V)

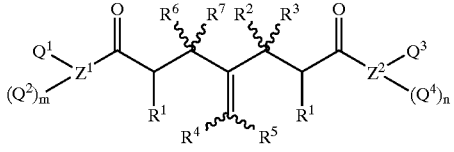
(VI)

is determined by the positioning or size of those substituents in the allylic reactant. That is, in allylic reactants having the structure (I)

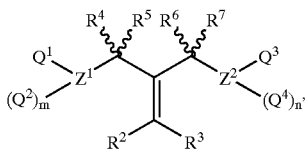
(I)

either (a) $R^2$ is cis to the carbon atom bound to $C(R^4R^5)$ and trans to the carbon atom bound to $C(R^6R^7)$, and $R^3$ is trans to the carbon atom bound to $C(R^4R^5)$ and cis to the carbon atom bound to $C(R^6R^7)$, or (b) the converse is true, i.e., $R^2$ is trans and $R^3$ is cis to the carbon atom bound to $C(R^4R^5)$ and so forth. The former compounds have the structure (Ia)

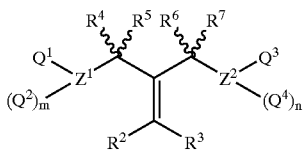
(Ia)

and the latter group of compounds have the structure (Ib)

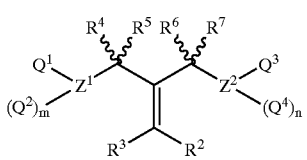
(Ib)

Assuming that $R^2$ is a sterically bulkier substituent than $R^3$, reaction of compound (Ia) with the acid chloride (IIa)

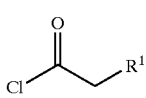
(IIa)

will give rise to the intermediates (IIa) and (IVa)

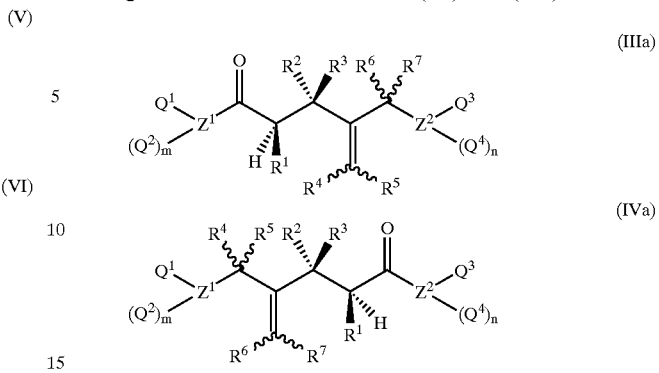
(IIIa)

(IVa)

while reaction of compound (Ib) with the acid chloride (IIa) gives rise to the intermediates (IIIb) and (IVb)

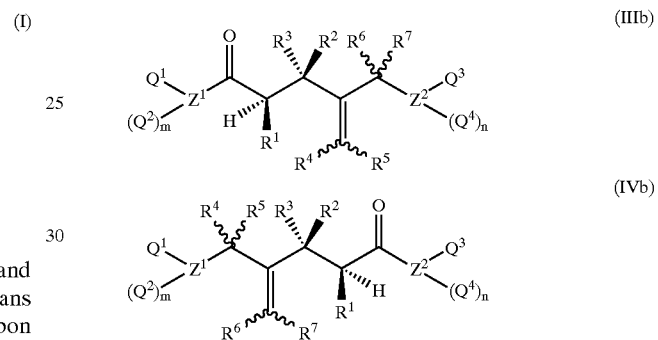
(IIIb)

(IVb)

Thus, a bulky $R^2$ substituent in a cis configuration would result in an anti configuration in relation to the $R^1$ substituent in the product, while a trans $R^2$ substituent would result in a syn configuration. Due to steric interactions, the syn configuration is selectively preferred and intermediates (IIb) and (IVb) will be the predominant intermediate species, i.e., a syn configuration of the sterically bulkier substituent of $R^2$ and $R^3$, and the substituent $R^1$ will be favored. Selectivity between the (IIIb) and (1Vb) intermediates may be achieved by utilizing different $Z^1Q^1(Q^2)_m$ and $Z^2Q^3(Q^4)n$ moieties. For example, should intermediate (IIIb) be preferred, $Z^1$ could be N and $Z^2$ could be S. The thioether moiety will be less reactive and Claisen rearrangement on the $Z^1$ side of the allylic reactant will be favored. The subsequent Claisen rearrangement on the $Z^2$ side of the allylic reactant may be facilitated by the use of a higher concentration of catalyst composition.

Analogously, the size and position of the $R^4$ and $R^5$ substituents in intermediate (IIIb) and the size and position of the $R^6$ and $R^7$ substituents in intermediate (IVb) determine the relative position of $R^4$ and $R^5$, or $R^6$ and $R^7$, in the final product. A sterically bulky $R^4$ or $R^5$, or $R^6$ or $R^7$, substituent will result in the positioning of that substituent in a syn configuration in relation to $R^8$ in the final product.

For example, assuming $R^4$ is a sterically bulkier substituent than $R^5$, intermediate (IIIb)

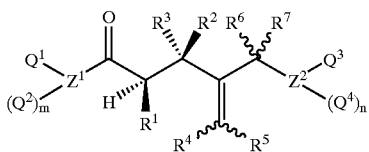

will give rise to the products (Va) and (Vb)

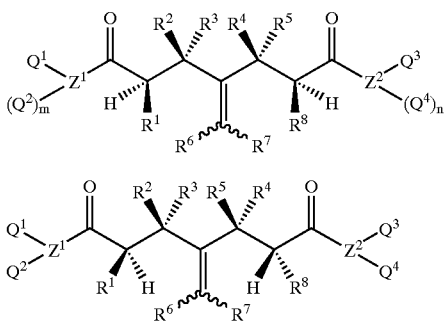

Similarly, assuming $R^6$ is bulkier than $R^7$, intermediate (IVb) will result in products (VIa) and (VIb)

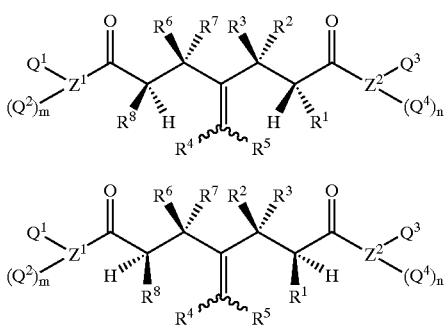

Looking at the four possible products above, it will be noted that in products (Va) and (VIa), the substituents $R^1$ and $R^8$ are in an anti configuration, while in products (Vb) and (VIb) they are in syn configuration. Steric interference prohibits the syn configuration from forming during the second Claisen rearrangement and, consequently, the anti configuration is highly preferred in the second reaction and the final product is a syn-anti configuration (e.g., syn between the bulkier substituent of the of the first rearrangement and the $R^1$ group of the acid chloride (IIa) and anti between the $R^1$ group of the acid chloride (IIa) and the $R^8$ group of the acid chloride (IIb)).

It is to be understood that while the invention has been described in conjunction with the preferred specific embodiments thereof, that the description above as well as the examples which follow are intended to illustrate and not limit the scope of the invention. Other aspects, advantages and modifications within the scope of the invention will be apparent to those skilled in the art to which the invention pertains.

All patents, patent applications, journal articles and other references cited herein are incorporated by reference in their entireties.

EXPERIMENTAL

In the following example, efforts have been made to ensure accuracy with respect to numbers used (e.g., amounts, temperature, etc.) but some experimental error and deviation should be accounted for. Unless indicated otherwise, temperature is in degrees C and pressure is at or near atmospheric.

General Information:

All non-aqueous reactions were performed using flame- or oven-dried glassware under an atmosphere of dry nitrogen. Commercial reagents were purified prior to use following the guidelines of Perrin and Armarego, Purification of laboratory Chemicals, Fourth Edition (Oxford, Butterworth-Heinemann, 1996). Non-aqueous reagents were transferred under nitrogen via syringe or cannula. Organic solutions were concentrated under reduced pressure on a Büichi rotary evaporator. Tetrahydrofuran and diethyl ether were distilled from sodium benzophenone ketyl prior to use. N,N-diisopropylethylamine and dichloromethane were distilled from calcium hydride prior to use. Air sensitive solids were dispensed in an inert atmosphere glovebox. Chromatographic purification of products was accomplished using forced-flow chromatography on ICN 60 32–64 mesh silica gel 63 according to the method of Still et al. (1978) J. Org. Chem. 43:2923. Thin-layer chromatography (TLC) was performed on EM Reagents 0.25 mm silica gel 60-F plates. Visualization of the developed chromatogram was performed by fluorescence quenching or $KMnO_4$ stain.

$^1H$ and $^{13}C$ NMR spectra were recorded on Bruker DRX-500 (500 MHZ and 125 MHZ, respectively), AMX-400 (400 MHZ and 100 MHZ), or AMX-300 (300 MHZ and 75 MHZ) instruments, as noted, and are internally referenced to residual protio solvent signals. Data for $^1H$ are reported as follows: chemical shift (δ ppm), multiplicity (s=singlet, d=doublet, t=triplet, q=quartet, m=multiplet), integration, coupling constant (Hz) and assignment. Data for $^{13}C$ are reported in terms of chemical shift. IR spectra were recorded on an ASI React-IR 1000 spectrometer and are reported in terms of frequency of absorption ($cm^{1-}$). Mass spectra were obtained from the UC Berkeley Mass Spectral facility. Gas chromatography was performed on Hewlett-Packard 5890A and 6890 Series gas chromatographs equipped with a split-mode capillary injection system and flame ionization detectors using the following columns: Bodman Chiraldex γ-TA (30 m×0.25 mm) and C&C Column Technologies CC-1701 (30 m×0.25 mm).

General Procedure A:

A round-bottomed flask containing $TiCl_4.(THF)_2$ was charged with a solution of the with the allyl morpholine in $CH_2Cl_2$, followed by i-$Pr_2NEt$. The reaction mixture was cooled to −20° C. for 5 min or unless otherwise noted maintained at room temperature before a solution of the acid chloride in $CH_2Cl_2$ was added dropwise over 1 min. The resulting dark red solution was stirred until the allyl morpholine was completely consumed (4–6 h) as determined by TLC (EtOAc). The reaction mixture was then diluted with EtOAc (20 mL) and washed with aqueous 1N NaOH (20 mL). The aqueous layer was then extracted with ethyl acetate (3×20 mL), and the combined organic layers washed with brine, dried ($Na_2SO_4$), and concentrated. The resulting residue was purified by silica gel chromatography (EtOAc) to afford the title compounds.

EXAMPLE 1

Synthesis of (2R*,3R*,6R*)-Trimethyl-4-methylene-1,7-dimorpholin-4-yl-heptane-1,7-dione Prepared according to General Procedure A using 1,3-dimorpholin-4-yl-2-ethylidenepropane 1 (50.0 mg, 0.208 mmol), $TiCl_4.(THF)_2$ (139 mg, 0.416 mmol), i-$Pr_2NEt$ (145

μL, 0.832 mmol), and propionyl chloride (0.62 mL, 1 M solution in $CH_2Cl_2$, 0.62 mmol) in 2.0 mL of $CH_2Cl_2$ at −20° C. to provide the pure product as a colorless oil in 93% yield (68.4 mg, 0.194 mmol); 94:6 syn-anti:syn-syn. Syn-anti isomer: IR ($CH_2Cl_2$) 2976, 2864, 1733, 1637, 1463, 1436, 1374, 1247, 1116, 1046 $cm^{-1}$; $^1$H NMR (400 MHZ, $CDCl_3$). 4.72 (s, 2H, $CH_2$=C), 3.43–3.68 (m, 16H,$O(CH_2CH_2)_2N$) 2.90 (m, 1H), 2.72 (m, 1H), 2.49 (dd, J=7.3, 14.6 Hz, 1H, $CH_2C$=$CH_2$), 2.36 (m, 1H), 2.0 (dd, J=6.4, 14.6, 1H, $CH_2C$=$CH_2$) 1.07 (d, J=6.5 Hz, 3H, $CH_3$), 1.04 (d, J=4.5 Hz, 3H, $CH_3$), 1.00 (d, J=6.3 Hz, 3H, $CH_3$); $^{13}$C NMR (100 MHZ). 174.7, 174.7, 152.2, 109.5, 67.0, 66.8, 46.1, 45.9, 42.1, 41.9, 40.6, 40.2, 40.0, 39.6, 33.4, 17.7, 17.3, 17.2, 15.3; LRMS (FAB) m/z 353 (MH)$^+$; HRMS (FAB) exact mass calcd for $(C_{19}H_{32}N_2O_4H)^+$ requires m/z 353.2440, found m/z 353.2444. Diastereomer ratio was determined by GLC with a CC-1701 column (100° C., 20° C./min gradient, 25 psi); syn-syn adduct $t_r$=32.7 min, syn-anti adduct $t_r$=33.4 min.

EXAMPLE 2

Synthesis of (2S*,3R*,6R*)-3-Chloro-2,6-dimethyl-4-methylene-1,7-di-morpholin-4-yl-heptane-1,7-dione Prepared according to General Procedure A using 2-chloromethylene-1,3-dimorpholin-4-yl-propane (80.0 mg, 0.307 mmol), $TiCl_4.(THF)_2$ (200 mg, 0.599 mmol), i-$Pr_2NEt$ (218 μL, 1.25 mmol), and propionyl chloride (0.94 mL, 1 M solution in $CH_2Cl_2$, 0.94 mmol) in 3.1 mL of $CH_2Cl_2$ at −20 ° C. to provide the pure product as a yellow oil in 93% yield (107 mg, 0.287 mmol); >95:5 syn-anti:syn-syn by $^1$H NMR. Syn-anti isomer: IR ($CH_2Cl_2$) 1640, 1463, 1436, 1235, 1116, 1031, 911 $cm^{-1}$; $^1$H NMR (400 MHZ, $CDCl_3$) δ 5.06 (s, 1H, $CH_2$=C), 4.89 (s, 1H, $CH_2$=C), 4.58 (d, J=12.5, 1H, CHCl) 3.46–3.68 (m, 16H, $O(CH_2CH_2)_2N$) 3.14 (dq, J=3.6, 6.8, 1H, CHCHCl) 2.98 (m, 1H, $COCHCH_2$), 2.58 (dd, J=8.4, 14.8 Hz, 1H, $CH_2C$=$CH_2$) 2.16 (dd, J=5.2, 14.8, 1H, $CH_2C$=$CH_2$) 1.34 (d, J=12.4 Hz, 3H, $CH_3$), 1.11 (d, J=6.8 Hz, 3H, $CH_3$); $^{13}$CNMR (100 MHZ) δ; 174.3, 172.0, 146.1, 114.5, 67.0, 66.9, 66.8, 66.6, 46.1, 42.1, 42.0, 40.9, 37.0, 36.6, 33.8, 18.2, 16.9; LRMS (FAB) m/z 373 (M)$^+$; HRMS (FAB) exact mass calcd for $(_{18}H_{29}ClN_2O_4)^+$ requires m/z 372.868, found m/z 373.1901.

EXAMPLE 3

Synthesis of (2S*,3R*,6R*)-2,6-Dimethyl4-methylene-3-phenylsulfanyl-1,7-di-morpholin-4-yl-heptane-1,7-dione Prepared according to General Procedure A using 1,3-dimorpholin-4-yl-2-phenylsulfanyl-propane (51.0 mg, 0.152 mmol), $TiCl_4.(THF)_2$ (102 mg, 0.305 mmol), i-$Pr_2NEt$ (112 μL, 0.608 mmol), and propionyl chloride (0.46 mL, 1 M solution in $CH_2Cl_2$, 0.46 mmol) in 1.5 mL of $CH_2Cl_2$ at −20 ° C. to provide the pure product as a yellow oil in 70% yield (47.8 mg,; 0.107 mmol); 93:7 syn-syn:syn-anti by $^1$H NMR Syn-anti isomer: IR (film) 3491, 2974, 2858, 1637, 1437, 1359, 1305, 1236, 1112, 1027, 896,742 $cm^{-1}$; $^1$H NMR (400 MHZ, $CDCl_3$) δ 7.37–7.40 (m, 2H, Ph) 7.21–7.29 (m, 3H, Ph) 4.73 (s, 1H, $CH_2$=C), 4.47 (s, 1H, $CH_2$=C) 3.84 (d, J=10.8 Hz, 1H, CHSPh) 3.39–3.68 (m, 16H, $O(CH_2CH_2)_2N$) 3.14 (dq, J=3.6, 6.8 Hz, 1H, CHCHSPh) 2.98 (m, 1H, (OC)$CHCH_2$), 2.58 (dd, J=8.4, 14.8 Hz, 1H, $CH_2C$=$CH_2$) 2.16 (dd, J=5.2, 14.8, 1H, $CH_2C$=$CH_2$) 1.34 (d, J=12.4 Hz, 3H, $CH_3$), 1.11 (d, J=6.8 Hz 3H, $CH_3$); $^{-C\ NMR}$ (100 MHZ) δ; 174.2, 173.2, 146.3, 134.7, 132.7, 128.7, 127.3, 112.2, 66.8, 66.6, 57.0, 45.9, 41.9, 38.7, 38.6, 33.6, 18.4, 17.2; LRMS (FAB) m/z 447 (MH)$^+$, HRMS (FAB) exact mass calcd for $(C_{24}H_{34}N_2O_4SH)^+$ requires m/z 447.23 18, found m 447 2315.

EXAMPLE 4

Synthesis of (2S*,3R*,6R*)-3Cyano2,6dimethyl-4-methylene-1,7-di-morpholin-4-yl-heptane-1,7-dione Prepared according to General Procedure A using 4-(-N-morpholinyl)-3(-N methyl-morpholinyl)-but-2-enenitrile (45.0 mg, 0.179 mmol), $TiCl_4.(THF)_2$ (120 mg, 0.359 mmol), i-$Pr_2NEt$ (125 μL, 0.716 mmol), and propionyl chloride (0.54 mL 1M solution $HC_2Cl_2$, 054 mmol) in 1.8 mL of $CH_2Cl_2$ at −20° C. to provide the pure product in 78% yield 5.7 mg, 0.139 mmol) as a white solid; mp 92–94 ° C.; 95:5 syn-anti:syn-syn by $^1$H NMR. Syn-anti isomer: IR (film)2974, 2920, 2858, 1637, 1444, 1359; 1112, 1074, 911, 850, 734 $cm^{-1}$; $^1$H NMR (400 MHZ, $CDCl_3$) δ 5.11 (s, 1H, $CH_2$=C), 4.95 (s, 1H, $CH_2$=C) 3.75 (d, J=9.2 Hz, 1H, CHCN) 3.47–3.67 (m, 16H, $O(CH_2CH_2)_2N$) 3.10 (dq, J=7.5, 15.3 Hz, 1H, (CHCHCN) 2.92 (m, 1H, (OC)$CHCH_2$), 2.54 (dd, J=8.6, 15.0 Hz, 1H, $CH_2C$=$CH_2$) 2.14 (dd, J=5.6, 15.2 Hz, 1H, $CH_2C$=$CH_2$) 1.30 (d, J=6.8 Hz, 3H, $CH_3$), 1.10 (d, J=6.8 Hz, 3H, $CH_3$), $^{13}$C NMR (100 MHZ) δ; 173.7, 171.0, 140.8, 116.1, 112.2, 66.8, 66.7, 66.6, 46.0, 45.9, 42.2, 42.0, 40.5, 37.8, 37.2, 33.6, 17.9, 16.4; LRMS (CI) m/z 363 (M)$^+$; HRMS (CI) exact mass calcd for $(C_{19}H_{29}N_3O_4)^+$ requires m/z 363.2158, found m/z 363.2162.

EXAMPLE 5

Synthesis of (2S*,3R*,6R*)-3-Benzoate 2,6-dimethyl-7methylene-1,7-di-morpholin-4-yl-heptane, 7-dione Prepared according to General Procedure A using benzoic acid-3-(-N-morpholinyl)-2-(-N-methyl-morpholinyl)-propenyl ester (50.0 mg, 0.144 mmol), $TiCl4.(THF)_2$ (96.4 mg, 0.289 mmol), i-$Pr_2NEt$ (100 μL, 0.576 mmol), and propionyl chloride (0.43 mL, 1 M solution in $CH_2Cl_2$, 0.43 mmol) in 2.9 mL of $CH_2Cl_2$ at rt to provide the pure product as a yellow oil in 80% yield (52.7 mg, 0.115 mmol); 89:11 syn-syn:syn-anti. Syn-anti isomer: IR )$CH_2Cl_2$) 2247, 1722, 1637, 1440, 1274, 1116, 1031, 703 $cm^{-1}$; $^1$H NMR (400 MHZ, $CDCl_3$) δ 8.06. (d, J=9.0 Hz, 2H, Ph,) 7.58 (t, J=9.3, 1H, Ph) 7.45 (t, J=9.5 Hz, 2H, Ph) 5.69 (d, J=9.5 Hz, 1H, CHOBz) 5.19 (s, 1H, $CH_2$=C), 4.98 (s, 1H, $CH_2$=C) 3.47–3.70 (m, 16H, $O(CH_2CH_2)_2N$) 3.25 (dt, J=8.5, 17.5 Hz, 1H, CHCHOBz) 3.02 (app dt, J=8.5, 20.4Hz, 1H, (CO)$CHCH_2$), 2:55 (dd, J=,9.0, 18.0 Hz, 1H, $CH_2C$= $CH_2$) 2.14 (dd, J=8.5, 18.0 Hz, 1H, $CH_2C$=$CH_2$) 1.24 (d, J=8.5 Hz, 3H, $CH_3$), 1.07 (d, J=8.5 Hz, 3H, $CH_3$); $^{13}$C NMR (100 MHZ) δ; 174.6, 171.7, 165.3, 145.1, 133.0, 130.0, 129.5, 128.4, 114.2, 76.0, 66.8, 46.2, 45.9, 42.1, 38.8, 37.4, 33.9, 17.7, 13.8; LRMS (CI) m/z 459 (MH)$^+$; HRMS (CI) exact mass calcd for $(C_{25}H_{34}N_2O_6H)^+$ requires m/z 459.2495, found m/z 459.2481.

EXAMPLE 6

Synthesis of (2R*,3S*,6R*)-4-Methylene-3-methyl-2,6-diphthalamido-1,7-dimorpholin-4-yl-heptane-1, 7-dione Prepared according to General Procedure A using 1 (52.7 mg, 0.219 mmol), $TiCl_4.(THF)_2$ (146 mg, 0.438 mmol), i-Pr$_2$NEt (0.31 mL, 1.8 mmol), and phthalylglycyl chloride (0.71 mL, 1 M solution in CH$_2$Cl$_2$, 0.71 mmol) in 4.4 mL of CH$_2$Cl$_2$ to provide the pure product as a light yellow solid in 74% yield (99.4 mg, 0.162 mmol); 94:16 syn-anti:syn-syn by $^1$H NMR. Syn-anti isomer: IR 2972, 2864, 2254, 1776, 1718, 1656, 1382, 1116, 923 cm$^{-1}$; $^1$H NMR (400 MHZ, CDCl$_3$) δ 7.86 (dd, J=3.2, 5.6 Hz, 2H, Phth) 7.84 (dd, J=3.0, 5.6 Hz, 2H, Phth) 7.72 (d, J=3.0 Hz, 2H, Phth) 7.70 (d, J=3.2 Hz, 2H, Phth) 5.42 (dd, J=4.4, 1.2 Hz, 1H, CH$_2$C=CH$_2$) 5.09 (s, 1H, CH$_2$=C), 5.0 (s, 1H, CH$_2$=C) 4.95 (d, J=10.4 Hz, 1H,) 3.40–3.90 (m, 16H, O(CH$_2$CH$_2$,)$_2$N) 2.98 (dd, J=3.7, 14.3 Hz, 1H) 0.89 (d, J=7.0 Hz, 3H, CH$_3$); $^{13}$C NMR (100 MHZ) δ; 173.9, 171.0, 140.8, 116.1, 112.2, 66.8, 66.7, 66.6, 46.0, 45.9, 42.2, 42.0, 40.5, 37.8, 37.2, 33.6, 17.9, 16.4; LRMS (FAB) m/z 614 (M)$^+$; HRMS (FAB) exact mass calcd for (C$_{33}$H$_{34}$N$_4$O$_8$)$^+$ requires m/z 615.2455, found m/z 615.2453.

EXAMPLE 7

Synthesis of (2S*,3R*,6S*)-2,6-Dibenzyl-4-methylene-3-methyl-1,7-dimorpholin-4-yl-heptane-1,7-dione Prepared according to General Procedure A using 1 (57.0 mg, 0.237 mmol), TiCl$_4$(THF)$_2$ (159 mg, 0.475 mmol), i-Pr$_2$NEt (165 μL, 0.948 mmol), and hydrocinnamoyl chloride (0.71 mL, 1 M solution in CH$_2$Cl$_2$, 0.71 mmol) in 2.4 mL of CH$_2$Cl$_2$ to provide the pure product as a white solid in 100% yield (120 mg, 0.237 mmol); mp 125–126° C.; 94:6 syn-anti:syn-syn. Syn-anti isomer: IR (CH$_2$Cl$_2$) 2974, 1637, 1444, 1236, 1120, 1035, 888 cm$^{-1}$; $^1$H NMR (500 MHZ, CDCl$_3$) δ 7.15–7.32 (m, 10H, Ph) 4.75(s, 1H, H$_2$C=C) 4.73 (s, 1H, H$_2$C=C) 3.71–3.78 (m, 1H) 3.60–3.66 (m, 1H) 3.53–3.57 (m, 1H) 3.45–3.49 (m, 1H) 3.36–3.40 (m, 1H) 3.18–3.34 (m, 5H) 3.06–3.15 (m, 3H) 2.90–3.06 (m, 1H) 2.96 (dd, J=2.9, 12.3 Hz, 1H) 2.75–2.91 (m, 5H) 2.62–2.70 (m, 1H) 2.54–2.61 (m, 2H) 2.46–2.51 (M, 1H) 2.23 (dd, J=5.5, 15.0 Hz, 1H) 1.23 (d, J=7.0 Hz, 3H, CH$_3$); $^{13}$C NMR (100 MHZ) δ; 173.1, 172.7, 139.6, 139.5, 129.1, 129.0, 128.4, 109.7, 66.8, 66.6, 66.4, 66.1, 65.9, 48.1, 45.9, 45.8, 41.9, 41.6, 41.5, 41.0, 39.6, 38.8, 37.2, 18.2; LRMS (FAB) m/z 505 (MH)$^+$; HRMS (FAB) exact mass calcd for (C$_{31}$H$_{40}$N$_2$O$_4$H)$^+$ requires m/z 505.3066, found m/z 505.3069. Diastereomer ratio was determined by HPLC with a 4.6×150 mm Hypersil column (45% EtOAc:He), syn-anti adduct t$_r$1.6 min and syn-syn adduct t$_r$=3.1 min.

EXAMPLE 8

Synthesis of (2R*,3S*,6R*)-3-Benzoate-4-methylene-2,6-dipivaloate-1,7-dimorpholin-4-yl-heptane-1,7-dione Prepared according to General Procedure A using benzoic acid-2-(-N-methyl-morpholine)-3-(-N-morpholinyl)-propenyl ester (74.0 mg, 0.214 mmol), TiCl$_4$.(THF)$_2$ (271 mg, 0.812 mmol), i-Pr$_2$NEt (0.30 mL, 1.7 mmol), and propionyl chloride (0.75 mL, 1 M solution in CH$_2$Cl$_2$, 0.75 mmol) in 4.2 mL of CH$_2$Cl$_2$ to provide the pure product as a colorless oil in 71% yield (95.9 mg, 0.152 mmol); 89:8:3 syn-anti:syn-syn:anti-syn; Syn-anti isomer: IR (film) 3059, 2981, 2255, 1730, 1661, 1452, 1267, 1151, 911, 718 cm$^{-1}$; $^1$H NMR (400 MHZ, CDCl$_3$) δ 7.98 (d, J=8.4, 2H, Ph) 7.57 (m, 1H, Ph) 7.44 (t, J=7.6, 2H, Ph) 5.77 (dd, J=8.0, 24.8 Hz, 1H) 5.56 (dd, J=6.0, 8.0 Hz, 1H) 5.46 (s, 1H, CH$_2$=C) 5.31 (s, 1H, CH$_2$=C) 3.53–3.82 (m, 16H, O(CH$_2$CH$_2$,)$_2$N) 2.63–2.65 (m, 2H) 1.11 (s, 18H, C(CH$_3$)$_3$); $^{13}$C NMR (125 MHZ) δ 177.6, 177.5, 168.1, 165.0, 164.8, 140.2, 133.4, 129.6, 129.2, 128.4, 118.9, 73.2, 69.8, 67.6, 66.7, 66.6, 46.2, 45.9, 42.4, 38.7, 38.4, 36.2, 26.8; LRMS (FAB) m/z 631 (MH)$^+$; HRMS (FAB) exact mass calcd for (C$_{33}$H$_{46}$N$_2$O$_{10}$H)$^+$ requires m/z 631.3231, found m/z 631.3237.

EXAMPLE 9

Synthesis of VMDIV-21:(2R*,3S*,6R*)-3-methyl-4-methylene-2,6dipivaloxy-1,7dimorpholin-4yl-heptane-1,7-dione Prepared according to General Procedure A using 1 (59.4 mg, 0.247 mmol), TiCl4.(THF)$_2$ (316 mg, 0.95 mmol), i-Pr$_2$NEt (0.34 mL, 2.0 mmol), and α-pivaloxyacetylchloride (0.86 mL, 1 M solution in CH$_2$Cl$_2$, 0.86 mmol) in 4.9 mL of CH$_2$C$_2$ to provide the pure product after purification by silica gel chromatography (85/15 EtOAc/He) as a yellow oil in 97% yield (126 mg, 0.240 mmol); >95:5 syn-anti:syn-syn by $^1$H NMR and $^{13}$C NMR. Syn-anti isomer: IR (film) 3059,2981, 1730, 1653, 1444, 1267, 1159, 911, 718 cm$^{-1}$; $^1$H NMR (400 MHZ, CDCl$_3$) δ 5.35 (dd, J=4.0, 9.6 Hz, 1H) 5.07 (d, J=8.0 Hz, 1H) 5.01 (s, 1H, CH$_2$=C) 4.99 (s, 1H, CH$_2$=C ) 3.39–3.61 (m, 16H, O(CH$_2$CH$_2$,)$_2$N) 2.68 (app t, J=7.4 Hz, 1H) 2.47(dd,J=9.8, 14.2Hz, 1H, CH$_2$=CCH$_2$) 2.37 (dd, J=3.8, 14.6Hz, 1H, CH$_2$=CCH$_2$) 1.15 (s, 9H, C(CH$_3$)$_3$) 1.14 (s, 9H, C(CH$_3$)$_3$ 1.06 (d, J=7.2 Hz, 3H, CH$_3$); $^{13}$C NMR (100 MHZ) δ 177.9, 177.7, 167.7, 167.7, 144.8, 115.4, 72.2, 67.4, 66.7, 46.3, 45.9, 42.4, 38.9, 38.6, 38.1, 27.0, 26.9, 16.3; LRMS (FAB) m/z 525 (MH)$^+$; HRMS (FAB) exact mass calcd for (C$_{27}$H$_{44}$N$_2$O$_8$H)$^+$ requires m/z 525.3176, found m/z 525.3175.

EXAMPLE 10

Synthesis of VMDIV-42:(2R*,3S*,6R*)-Chloro-4-methylene-2,6-dipivaloxy-1,7-dimorpholin-4-yl-heptane-1,7-dione Prepared according to the General Procedure A using 2-chloromethylene-1,3-dimorpholin-4-yl-propane (77.0 mg, 0.295 mmol), TiCl$_4$.(THF)$_2$ (374 mg, 1.12 mmol), i-Pr$_2$NEt (0.41 mL, 2.4 mmol), and α-pivaloxyacetylchloride (1.0 mL, 1 M solution in CH$_2$Cl$_2$, 1.0 mmol) in 6.0 mL of CH$_2$Cl$_2$ to provide the pure product as an orange oil in 84% yield (135 mg, 0.248 mmol); >95:5 syn-anti:syn-syn by $^1$H NMR and $^{13}$C NMR. Syn-anti isomer: IR (film) 2974, 2927, 2866, 1730, 1653, 1452, 1274, 1151, 1074, 1027 cm$^{-1}$; $^{-1}$H NMR (300 MHZ) 5.62 (d, J=9.2Hz, 1 H, CHCHCl) 5.49 (t, J=7.0 Hz, 1 H, (OC)CHCH$_2$) 5.39 (s, 1H, H$_2$C=C) 5.25 (s, H$_2$C=C) 4.83 (d, J=9.2 Hz, 1H, CHCl) 3.40–3.70 (m, 16H, O(CH$_2$CH$_2$)$_2$N) 2.63 (app dd, J=6.9 Hz, 2H, H$_2$C=CCH$_2$) 1.22 (d, J=9.0 Hz, 3H, CH$_3$); $^{13}$C. NMR (125 MHZ) 177.8, 177.4, 167.5, 165.2, 139.9, 120.1, 70.7, 67.4, 66.7, 66.6, 61.2, 59.8, 46.0, 42.6, 42.5, 38.9, 38.6, 36.0, 35.8, 27.0, 20.9, 20.3; LRMS (FAB) m/z 545 (MH)$^+$; FIRMS (FAB) exact mass calcd for (C$_{26}$H$_{41}$ClN$_2$O$_8$H)$^+$ requires m/z 545.2736.

We claim:

1. A method for conducting a tandem Claisen rearrangement reaction, comprising reacting an allylic reactant with at least one acid chloride in the presence of a Lewis acid catalyst composition comprising a first catalyst component composed of a Lewis acid, and a second catalyst component selected from the group consisting of tertiary amines and non-nitrogenous bases, wherein the allylic reactant is semi-nally di-substituted with a first substitute —C(R$^4$R$^5$)—Z$^1$Q$^1$ (Q$^2$)$_m$ and a second substituent —C(R$^6$R$^7$)—Z$^2$Q$^3$(Q$^4$)$_u$, wherein:

$R^4$, $R^5$, $R^6$, and $R^7$ are independently selected from the group consisting of hybrido, halo, hydroxyl, sulfhydryl, amino, substituted amino, hydrocarbyl, substituted hydrocarbyl, heteroatoms-containing hydrocarbyl, and substituted heteroatom-containing hydrocarbyl;

$Z^1$ and $Z^2$ are independently N, O or S;

m is zero or 1, with the proviso that when $Z^1$ is N, m is 1, and when $Z^1$ is S or O, m is zero;

n is zero or 1, with the further proviso that when $Z^2$ is N, n is 1, and when $Z^2$ is S or O, n is zero; and $Q^1$, $Q^2$, $Q^3$ and $Q^4$ are independently selected from the group consisting of hydrocarbyl, substituted hydrocarbyl, heteroatom-containing hydrocarbyl, and substituted heteroatoms-containing hydrocarbyl, or, when $Z^1$ is N and m is 1, $Q^1$ and $Q^2$ are joined together in a ring structure or together with $Z^1$ form an azide group, or, when $Z^2$ is N and n is 1, $Q^3$ and $Q^4$ are joined together in a ring structure or together with $Z^2$ form an azide group, and further wherein the molar ratio of acid chloride to the allylic reactant is selected to enable the reactant to undergo at least two successive Claisen rearrangement reactions.

2. The method of claim 1, wherein the allylic reactant is selected from the group consisting of allylic amines, allylic thioethers, and allylic ethers.

3. The method of claim 2, wherein the allylic reactant is an allylic amine.

4. The method of claim 3, wherein the allylic reactant is an allylic diamine.

5. The method of claim 4, wherein the allylic diamine contains two tertiary amine groups.

6. The method of claim 1, wherein the acid chloride is a 2-substituted acetyl chloride.

7. The method of claim 1, wherein the reaction is carried out under inert, nonaqueous conditions.

8. The method of claim 1, wherein the reaction is carried out at a temperature in the range of approximately −110° C. to 200° C.

9. The method of claim 8, wherein the reaction is carried out at a temperature in the range of approximately −78° C. to 100° C.

10. The method of claim 1, wherein one of the allylic reactant, the acid chloride and the catalyst composition is covalently linked, either directly or indirectly, to the surface of a solid support.

11. The method of claim 1, wherein the second catalyst component is a tertiary amine.

12. The method of claim 1, wherein the second catalyst component is a non-nitrogenous base.

13. The method of claim 1, wherein the size and/or positioning of substituents on the allylic reactant results in an enantioselective reaction.

14. The method of claim 1, wherein the allylic reactant has the structure of formula (I)

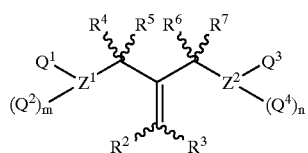

(I)

and the at least one acid chloride comprises a first acid chloride having the structure of formula (IIa) and a second acid chloride has the structure of formula (IIb)

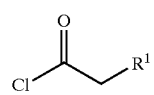

(IIa)

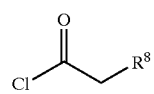

(IIb)

wherein $R^4$, $R^5$, $R^6$, $R^7$, $Z^1$, $Z^2$, m, n, $Q^1$, $Q^2$, $Q^3$ and $Q^4$ are as defined previously, and $R^1$, $R^2$, $R^3$, and $R^8$ are independently selected from the group consisting of hydrido, halo, hydroxyl, sulfhydryl, amino, substituted amino, hydrocarbyl, substituted hydrocarbyl, heteroatom-containing hydrocarbyl, and substituted heteroatom-containing hydrocarbyl, wherein when $R^1$ and $R^8$ are identical, reaction is carried out with a single acid chloride, resulting in a reaction product having the structure of formula (V) or (VI)

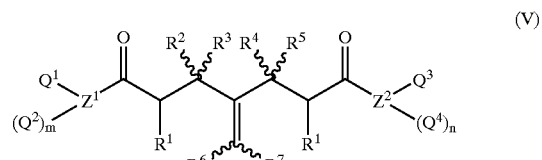

(V)

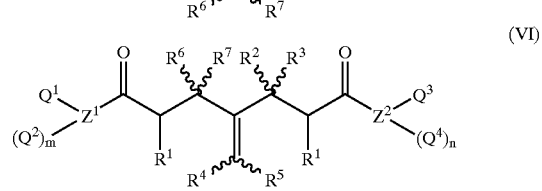

(VI)

15. The method of claim 14, wherein the first catalyst component has the structural formula (VII)

(VII)

wherein M is a metal, X is a halide, a halide-containing group, lower alkoxy, fluorinated lower alkoxy, sulfate, acetate, trifluoroacetate or triflate, Y is hydrocarbyl, substituted hydrocarbyl, heteroatom-containing hydrocarbyl, substituted heteroatom-containing hydrocarbyl, or an oxygen-containing or nitrogen-containing organic ligand, a is an integer of 1 or more, and the sum of a and b is in the range of 2 to $n_{max}$, where $n_{max}$ is the number of atoms that can bind to M through single covalent or coordination bonds.

16. The method of claim 15, wherein M is selected from the group consisting of Groups 2 through 13 of the Periodic Table of the Elements.

17. The method of claim 16, wherein M is selected from the group consisting of Ti, Mg, Al, Sc, Y, Ni, Cu, Zn and Yb.

18. The method of claims 17, wherein M is selected from the group consisting of Ti, Mg and Al.

19. The method of claim 15 wherein a is at least 2.

20. The method of claim 18, wherein X is a halide or triflate.

21. The method of claim 19, wherein Y is a nitrogen-containing ligand.

22. The method of claim 20, wherein Y has the structure of formula (VIIIa) or (VIIIb)

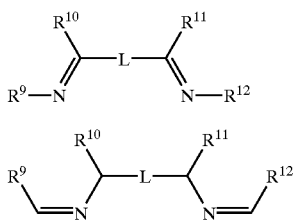

(VIIIa)

(VIIIb)

wherein L is a hydrocarbylene, substituted hydrocarbylene, heteroatom-containing hydrocarbylene, substituted heteroatom-containing hydrocarbylene or heteroatom linkage, and $R^9$, $R^{10}$, $R^{11}$ and $R^{12}$ are independently selected from the group consisting of hydrido, halo, hydroxyl, sulfhydryl, amino, substituted amino, hydrocarbyl, substituted hydrocarbyl, heteroatom-containing hydrocarbyl, and substituted heteroatom-containing hydrocarbyl, or wherein $R^9$ and $R^{10}$ and/or $R^{11}$ and $R^{12}$ may be linked to form a hydrocarbylene, substituted hydrocarbylene, heteroatom-containing hydrocarbylene, or substituted heteroatom-containing hydrocarbylene bridge.

23. The method of claim 22, wherein Y has the structure of formula (IXa) or (IXb)

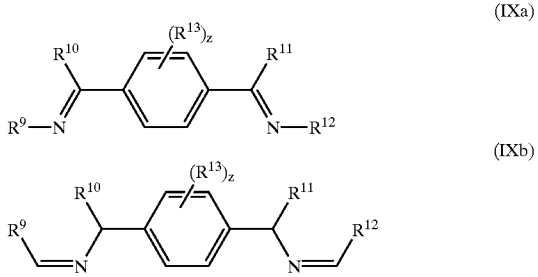

wherein $R^{13}$ is as defined for $R^9$, $R^{10}$, $R^{11}$ and $R^{12}$, and z is an integer in the range of zero to 5 inclusive.

24. The method of claim 23, wherein Y has the structure of formula (IXa).

25. The method of claim 24 wherein Y has the structure of formula (X)

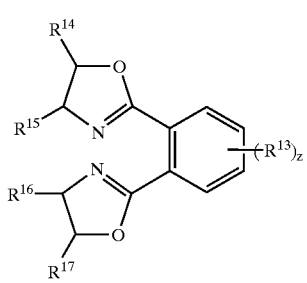

wherein $R^{14}$, $R^{15}$, $R^{16}$ and $R^{17}$ are defined as for $R^{13}$.

26. The method of claims 14, wherein the second catalyst component is a tertiary amine.

27. The method of claim 26, wherein the tertiary amine has the structure $NR^{18}R^{19}R^{20}$ wherein $R^{18}$, $R^{19}$ and $R^{20}$ are independently hydrocarbyl, substituted hydrocarbyl, heteroatom-containing hydrocarbyl or substituted heteroatom-containing hydrocarbyl, or wherein two of $R^{18}$, $R^{19}$ and $R^{20}$ are linked to form a hydrocarbylene, substituted hydrocarbylene, heteroatom-containing hydrocarbylene or substituted heteroatom-containing hydrocarbylene bridge.

28. The method of claim 27, wherein the tertiary amine is a trialkylamine.

29. The method of 28, wherein the tertiary amine is a tri(lower alkyl)amine.

30. The method of claim 26, wherein the tertiary amine is comprised of a nitrogen-containing heterocycle in which at least one nitrogen heteroatom is in the form —N═.

31. The method of claims 14, wherein the second catalyst component is a non-nitrogenous base.

32. The method of claim 31 wherein the non-nitrogenous base is selected from the group consisting of inorganic hydroxides, inorganic oxides, and metal carbonates.

33. The method of claim 32, wherein the non-nitrogenous base is selected from the group consisting of sodium hydroxide, potassium hydroxide, sodium carbonate and potassium carbonate.

34. The method of claim 14, wherein the molar ratio of the allylic reactant to the acid chloride is approximately 1:N, where N is the number of functional groups on the allylic reactant that enable the reactant to undergo Claisen rearrangement reactions.

35. The method of claim 34, wherein N is 2.

36. The method of claim 14, wherein the reaction is carried out under inert, nonaqueous conditions.

37. The method of claim 14, wherein the reaction is carried out at a temperature in the range of approximately −11020 C. to 200° C.

38. The method of claim 37, wherein the reaction is carried out at a temperature in the range of approximately −78° C. to 100° C.

39. The method of either claim 14 or claim 15, wherein one of the allylic reactant, the acid chloride and the catalyst composition is covalently linked, either directly or indirectly to the surface of a solid support.

40. The method of either claim 14 or claim 17, wherein the size and/or positioning of substituents on the allylic reactant results in an enantioselective reaction.

41. The method of claim 14, wherein $R^1$ and $R^8$ are identical, such that reaction of the allylic reactant is carried out with a single acid chloride.

* * * * *

UNITED STATES PATENT AND TRADEMARK OFFICE
CERTIFICATE OF CORRECTION

PATENT NO. : 6,552,226 B1
DATED : April 22, 2003
INVENTOR(S) : David W.C. MacMillan It is certified that error appears in the above-identified patent and that said Letters Patent is hereby corrected as shown below:

Column 26,
Lines 64 and 65, claim 1, please delete "semi-nally" and replace with -- geminally --
Line 65, please delete "substitute" and replace with -- substituent --
Line 66, please delete $(Q^4)_u$" and replace with -- $(Q^4)_n$ --

Column 27,
Lines 4 and 14, please replace "heteroatoms" and replace with -- heteroatom --

Column 28,
Lines 25 - 31, in structure (V), please delete "$R^1$" and replace with -- $R^8$ --.
The corrected structure will appear as follows:

(V)
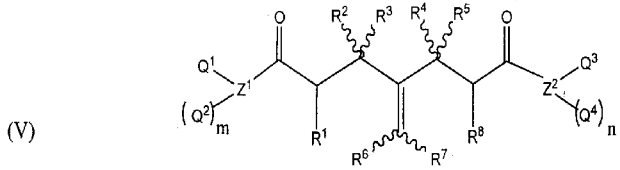

Lines 32 - 38, in structure (VI), please delete "$R^1$" and replace with -- $R^8$ --.
The corrected structure will appear as follows:

(VI)
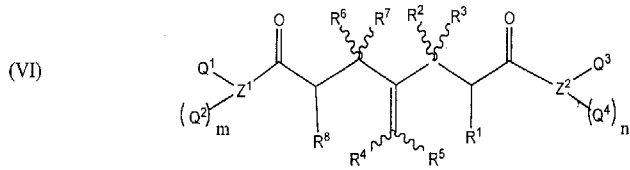

UNITED STATES PATENT AND TRADEMARK OFFICE
CERTIFICATE OF CORRECTION

PATENT NO.    : 6,552,226 B1
DATED         : April 22, 2003
INVENTOR(S)   : David W.C. MacMillan It is certified that error appears in the above-identified patent and that said Letters Patent is hereby corrected as shown below:

<u>Column 30,</u>
Lines 1 and 20, please delete "claims" and replace with -- claim --
Line 42, please delete "-1120 C." and replace with -- 110° C --
Line 50, please delete "claim 17" and replace with -- claim 15 --
After line 56, please add claims 42 and 43 as follows:

-- 42. The method of claim 1, wherein the molar ratio of the allylic reactant to the acid chloride is approximately 1:N, where N is the number of functional groups on the allylic reactant that enable the reactant to undergo Claisen rearrangement reactions.

43. The method of claim 42, wherein N is 2. --

Signed and Sealed this

Sixteenth Day of September, 2003

JAMES E. ROGAN
*Director of the United States Patent and Trademark Office*